(12) United States Patent
Rambo

(10) Patent No.: US 6,613,952 B2
(45) Date of Patent: Sep. 2, 2003

(54) O-RING FOR INCREMENTALLY ADJUSTABLE INCISION LINER AND RETRACTOR

(76) Inventor: Robert D. Rambo, 702 Simmons Rd., Sellersville, PA (US) 18960

(*) Notice: Subject to any disclaimer, the term of this patent is extended or adjusted under 35 U.S.C. 154(b) by 0 days.

(21) Appl. No.: 10/196,647

(22) Filed: Jul. 16, 2002

(65) Prior Publication Data

US 2003/0062051 A1 Apr. 3, 2003

Related U.S. Application Data

(63) Continuation of application No. 09/970,416, filed on Oct. 3, 2001, now Pat. No. 6,450,983.

(51) Int. Cl.[7] .............................................. A61F 13/00
(52) U.S. Cl. ........................ 602/41; 602/60; 600/206; 600/208
(58) Field of Search .............................. 128/845, 846, 128/888; 602/42, 43, 50, 60, 63, 75, 901; 600/206, 207, 208, 236

(56) References Cited

U.S. PATENT DOCUMENTS

| | | |
|---|---|---|
| 2,305,289 A | 12/1942 | Coburg |
| 3,347,226 A | 10/1967 | Harrower |
| 3,347,227 A | 10/1967 | Harrower |
| 4,975,247 A | 12/1990 | Badolato et al. |
| 5,514,133 A | 5/1996 | Golub et al. |
| 5,524,644 A | 6/1996 | Crook |
| 5,640,977 A | 6/1997 | Leahy et al. |
| 5,649,550 A | 7/1997 | Crook |
| 5,769,794 A | 6/1998 | Conlan et al. |
| 5,810,721 A | 9/1998 | Mueller et al. |
| 5,813,409 A | 9/1998 | Leahy et al. |
| 5,906,577 A | 5/1999 | Beane et al. |
| 5,957,913 A | 9/1999 | de la Torre et al. |
| 6,024,736 A | 2/2000 | de la Torre et al. |
| 6,033,426 A | 3/2000 | Kaji |
| 6,042,573 A | 3/2000 | Lucey |
| 6,048,309 A | 4/2000 | Flom et al. |
| 6,142,935 A | 11/2000 | Flom et al. |
| 6,142,936 A | 11/2000 | Beane et al. |
| 6,149,642 A | 11/2000 | Gerhart et al. |
| 6,254,533 B1 | 7/2001 | Fadem et al. |
| 6,254,534 B1 | 7/2001 | Butler et al. |
| 6,382,211 B1 | 5/2002 | Crook |
| 2001/0037053 A1 | 3/2001 | Bonadio et al. |

Primary Examiner—Nicholas D. Lucchesi
Assistant Examiner—Lalita M. Hamilton
(74) Attorney, Agent, or Firm—Duane Morris LLP

(57) ABSTRACT

An O-ring is provided for use in an adjustable surgical wound protector having a solid cross-section including a cross-sectional center that is spaced from a central longitudinal axis and a resilient configuration for squeezing into an oblong shape that is insertable into a surgical incision. At least one recess is defined in the O-ring that is selectively sized and shaped to enable a snap-action rolling of the O-ring about the cross-sectional center in predetermined increments. The recess may comprise various cross-sectional shapes, such as, at least one circumferential groove, a plurality of circumferentially positioned recesses, or be shaped such that the O-ring comprises a cruciform cross-section. An improved incrementally adjustable apparatus for protecting an incised wound from exposure to bacterial and other harmful contaminants is also provided including a pair of resilient O-rings connected to opposite ends of an impermeable pliable sleeve. One of the O-rings is formed to engage the inner edge of the wound with a portion of the sleeve above the wound capable of being rolled onto the other ring to draw the remaining sleeve portion contiguous with the sides of the wound.

9 Claims, 24 Drawing Sheets

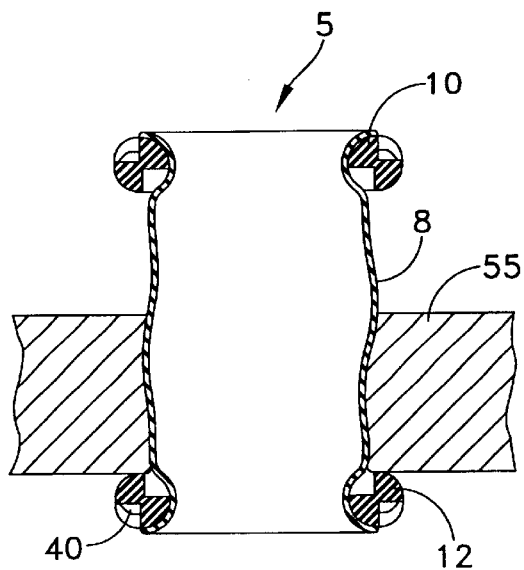
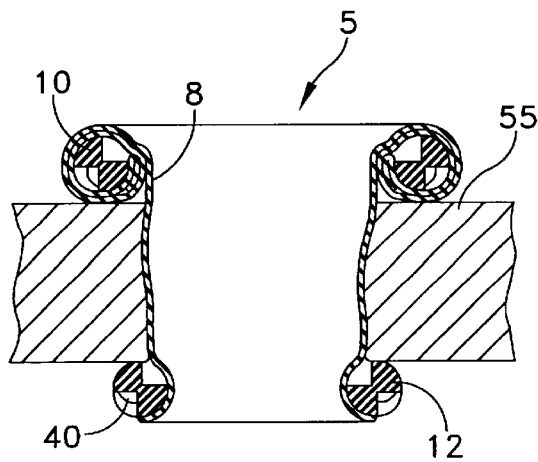
FIG. 6  FIG. 7
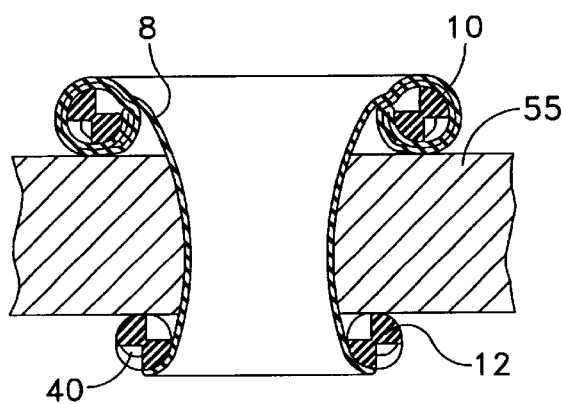
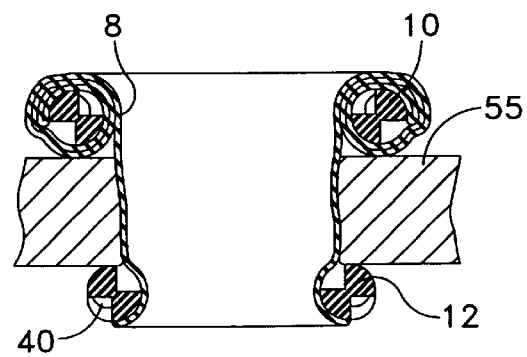
FIG. 8  FIG. 9

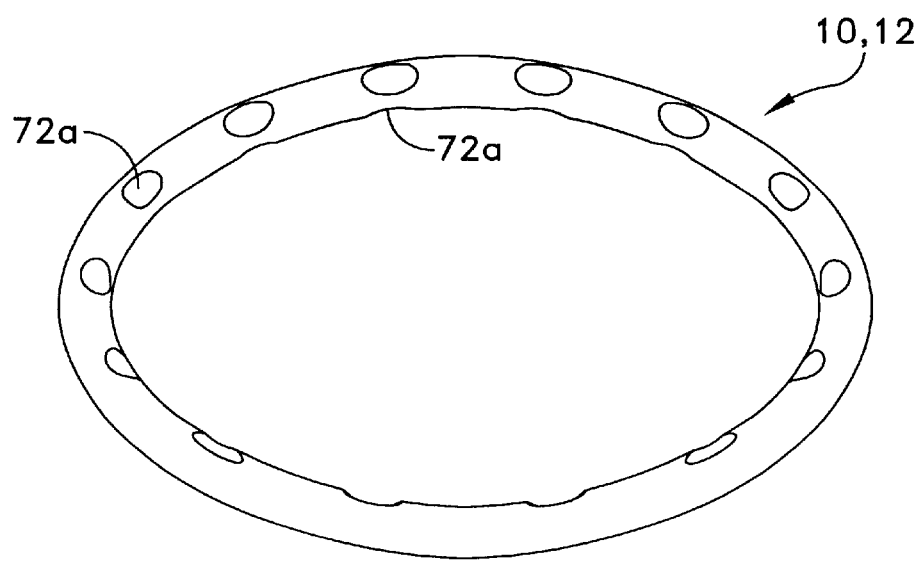
FIG. 22
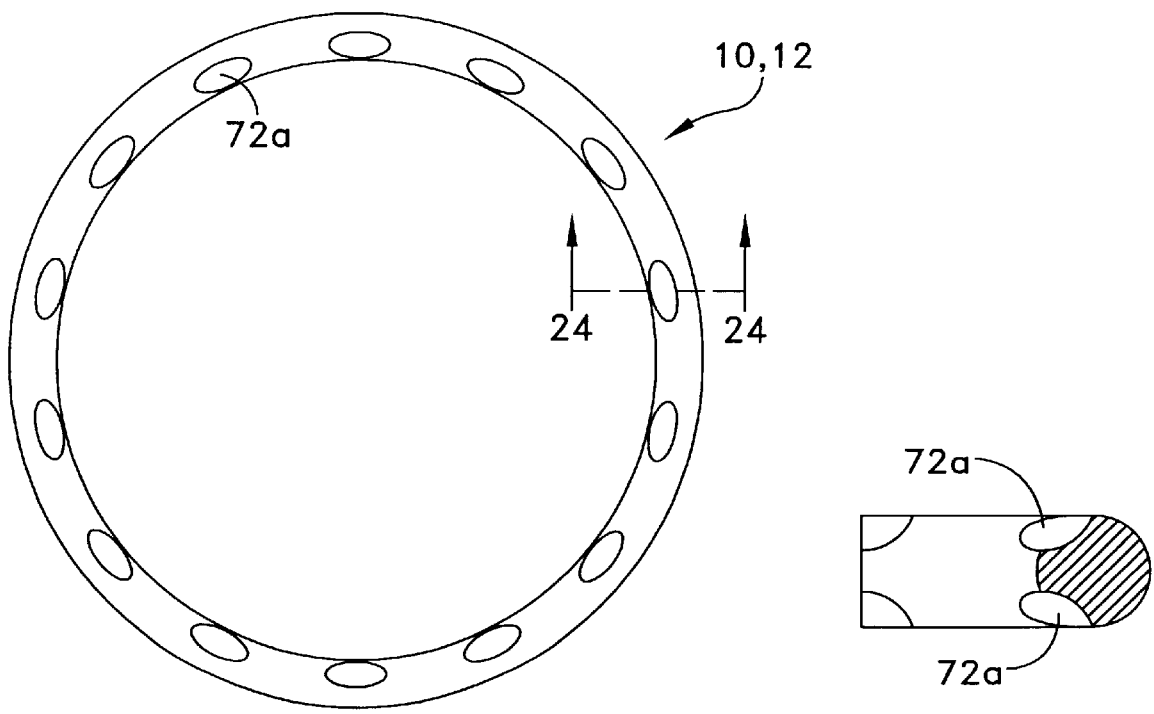
FIG. 23
FIG. 24

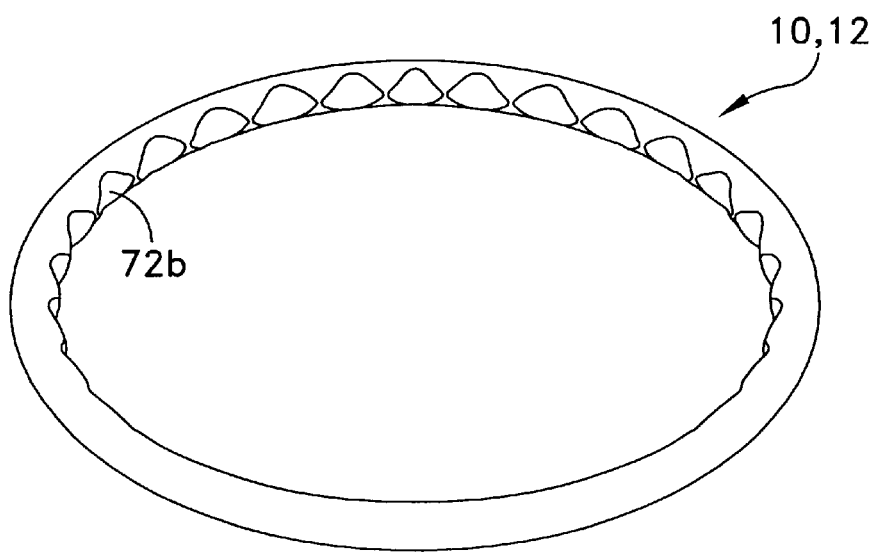
FIG. 25
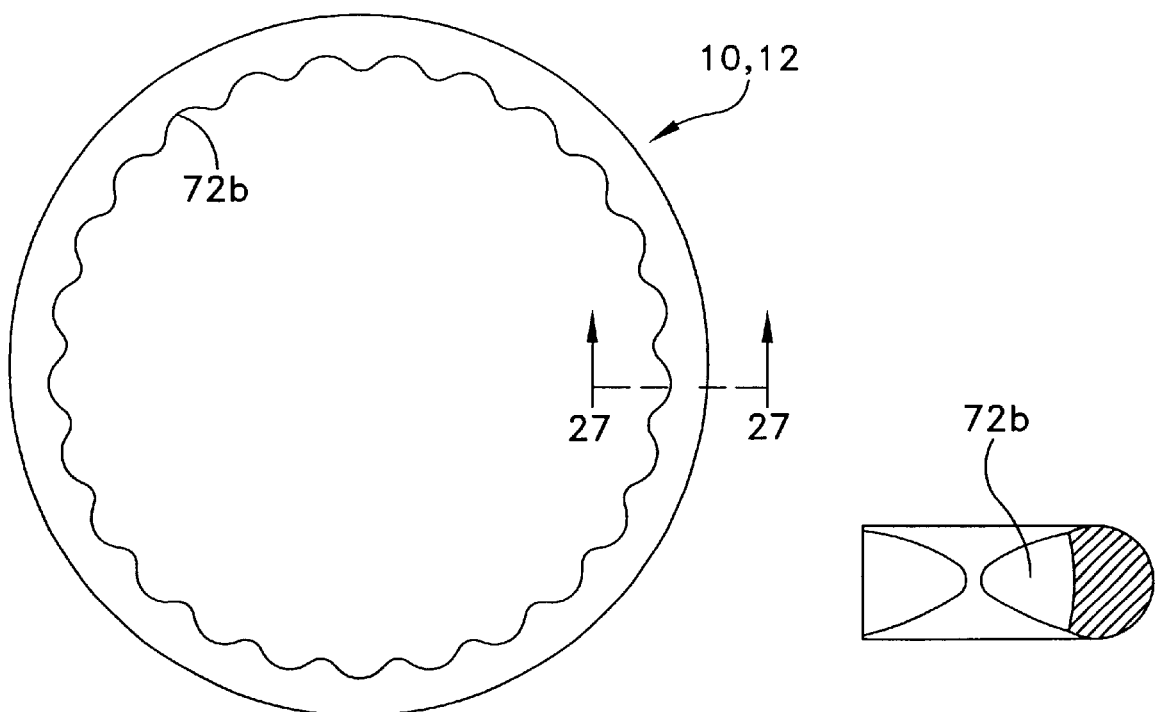
FIG. 26
FIG. 27

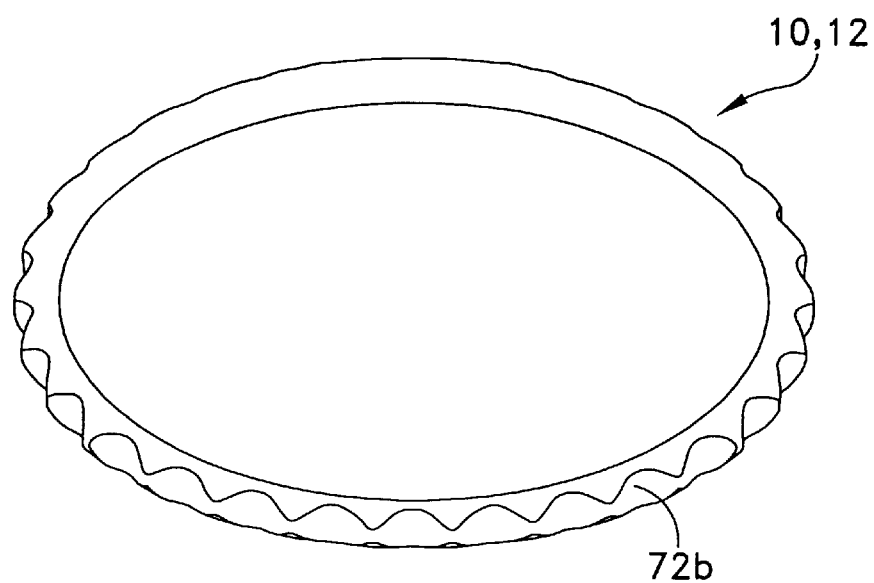
FIG. 28
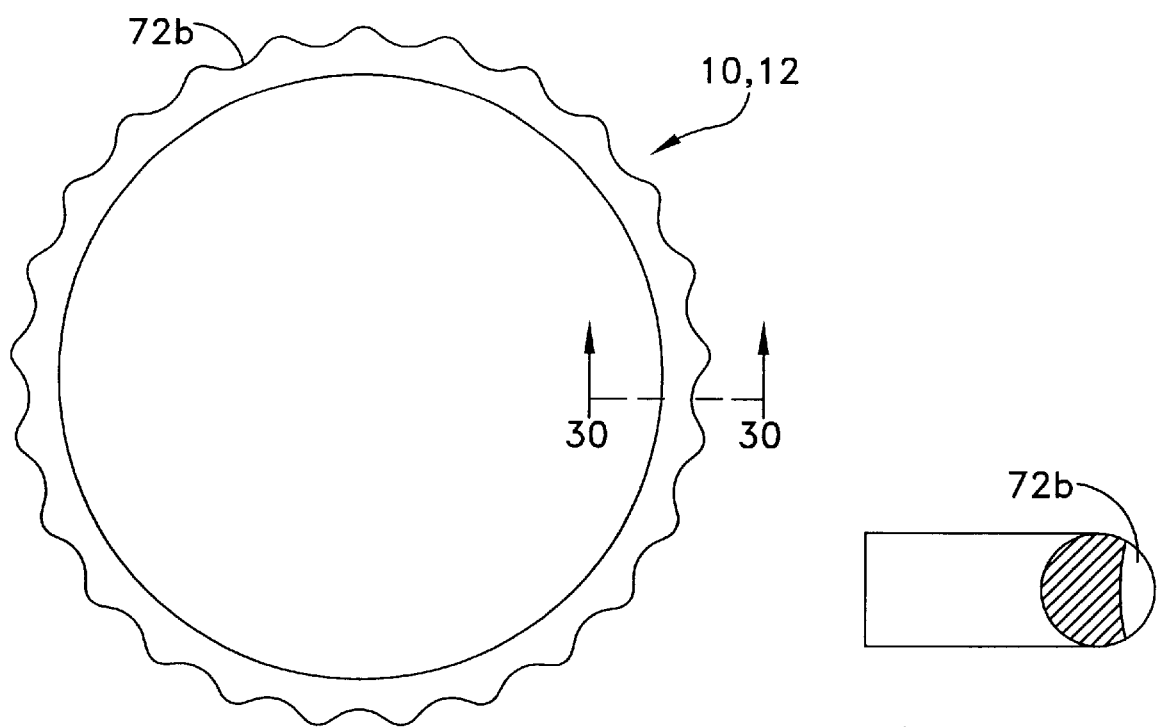
FIG. 29
FIG. 30

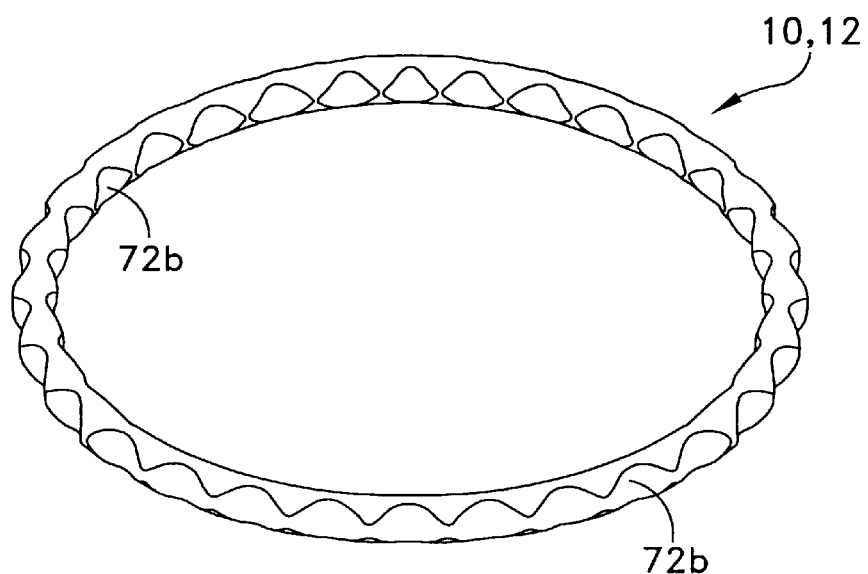
FIG. 31
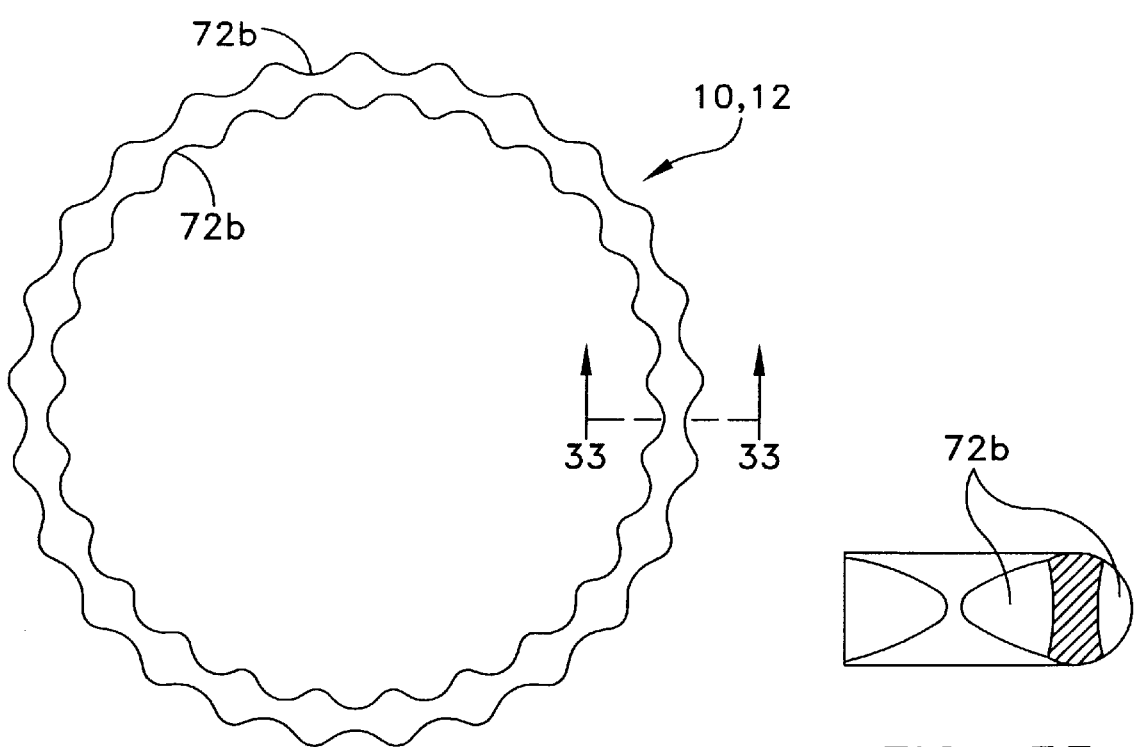
FIG. 32
FIG. 33

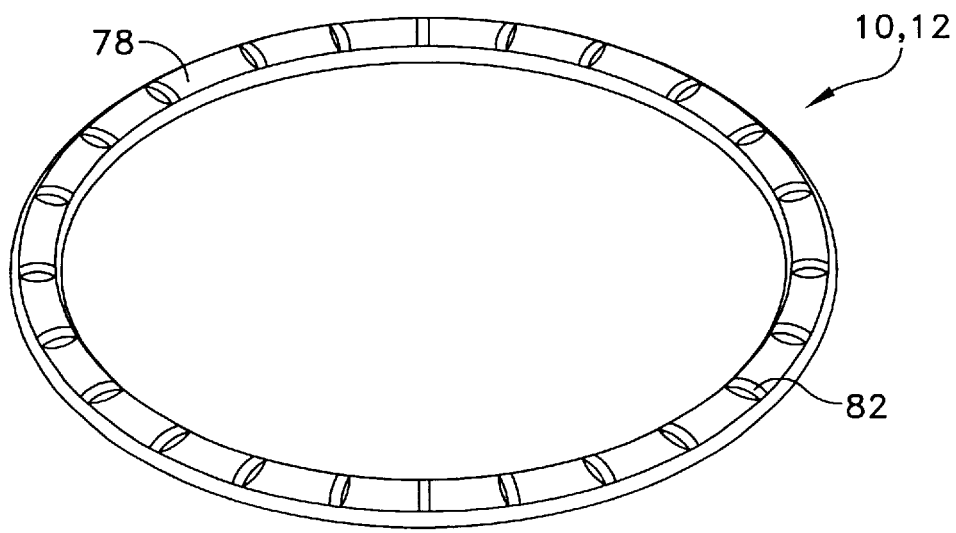
FIG. 40
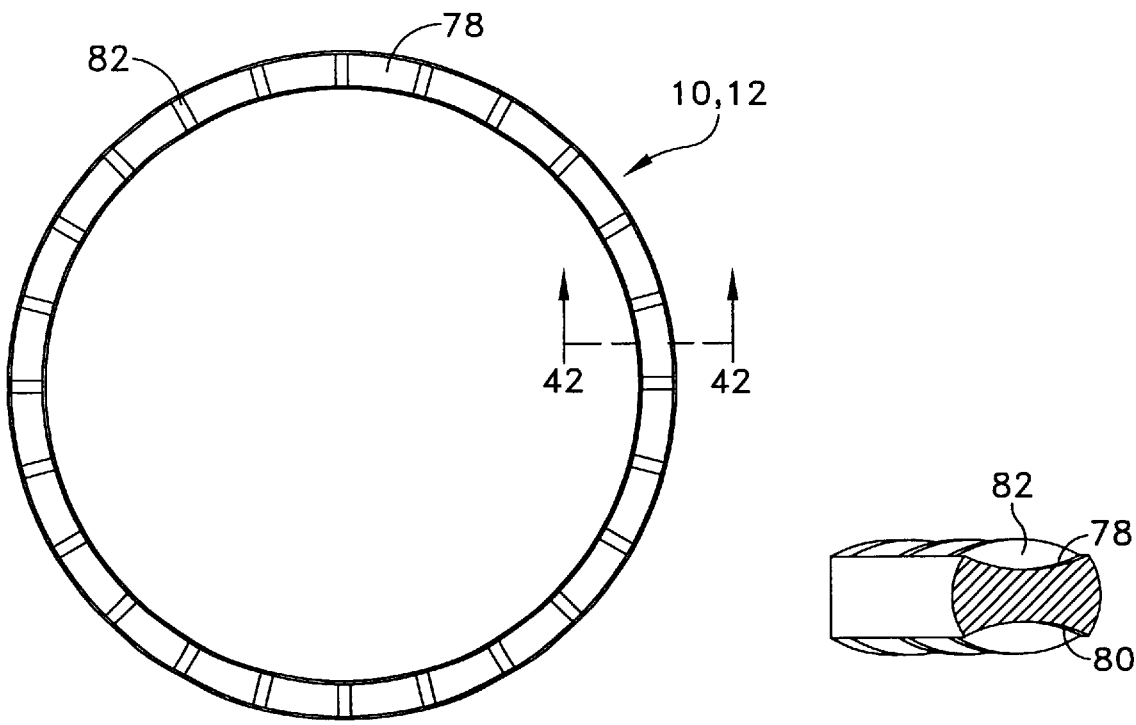
FIG. 41
FIG. 42

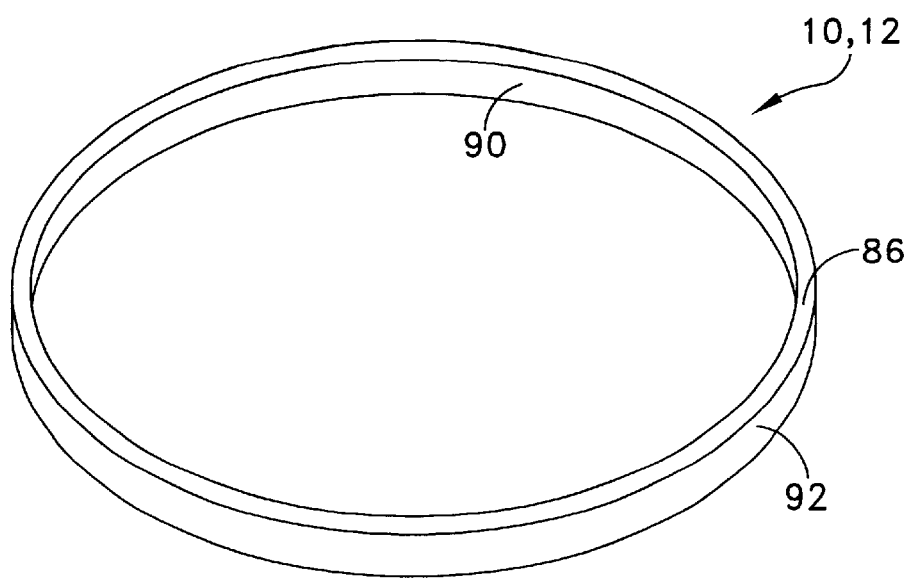
FIG. 43
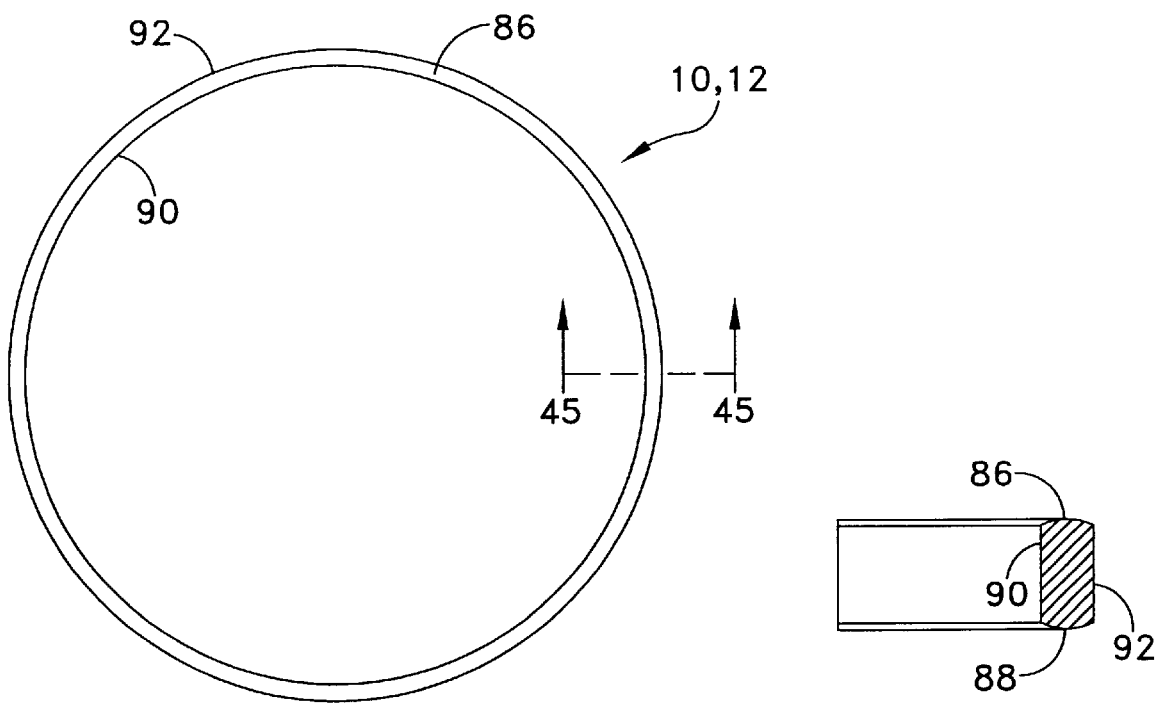
FIG. 44
FIG. 45

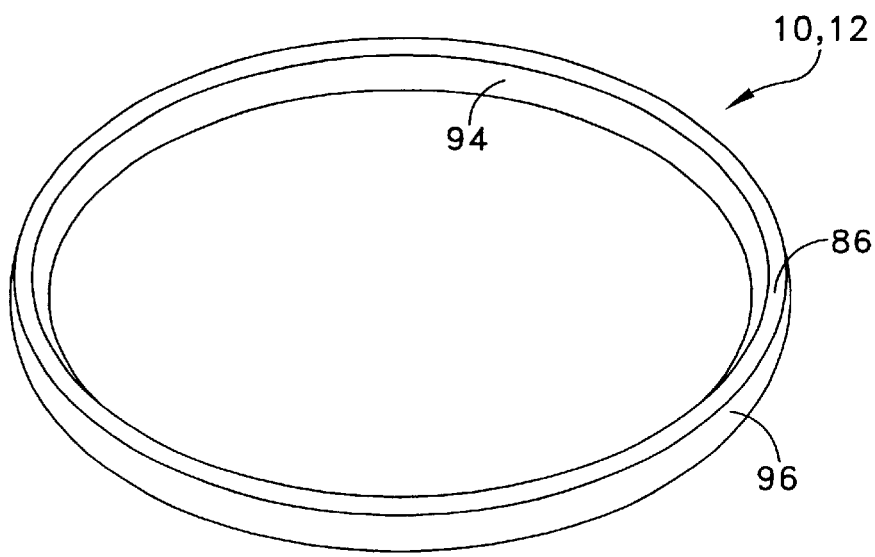
FIG. 46
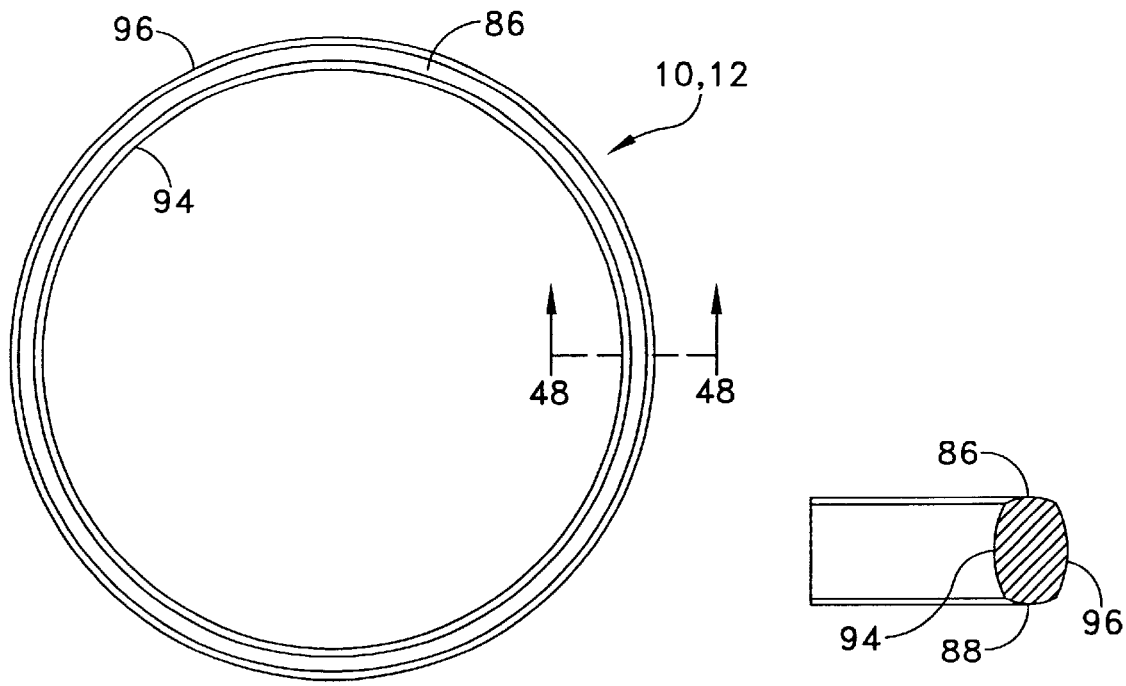
FIG. 47
FIG. 48

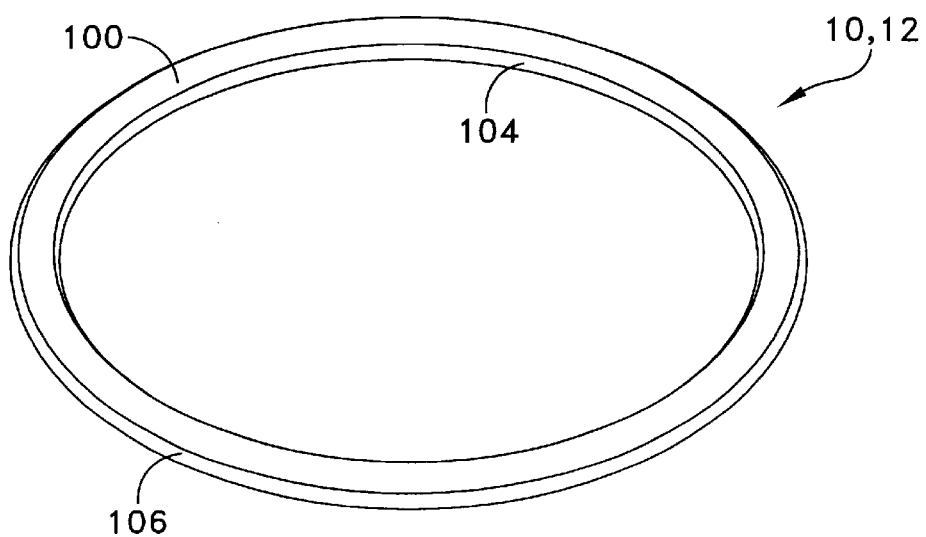
FIG. 49
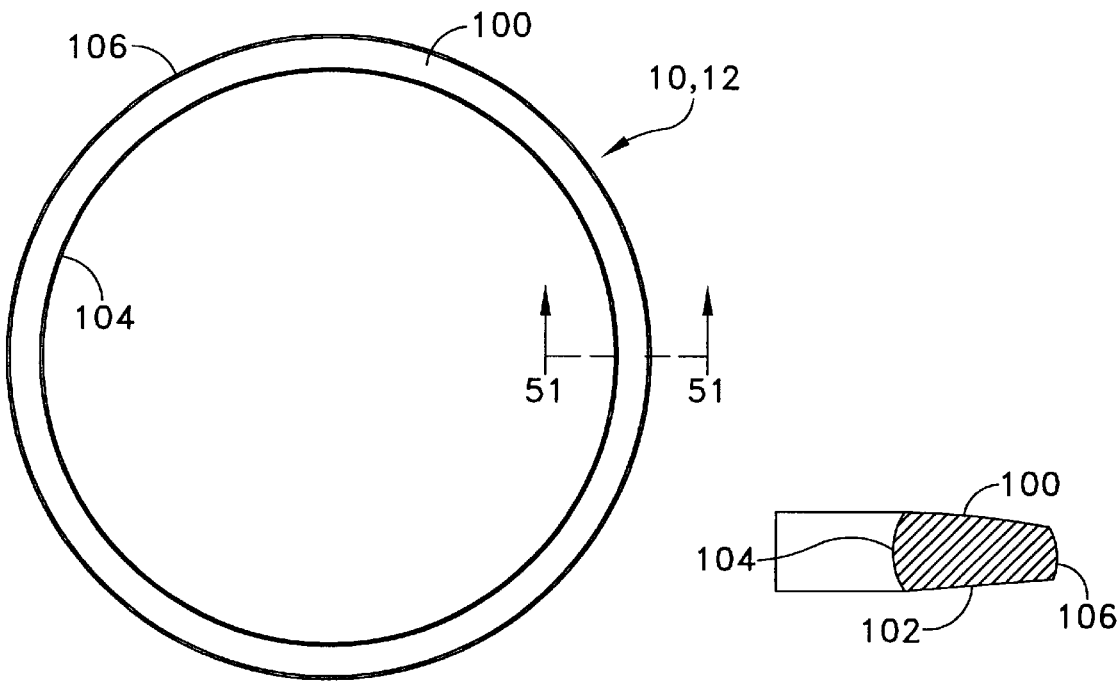
FIG. 50
FIG. 51

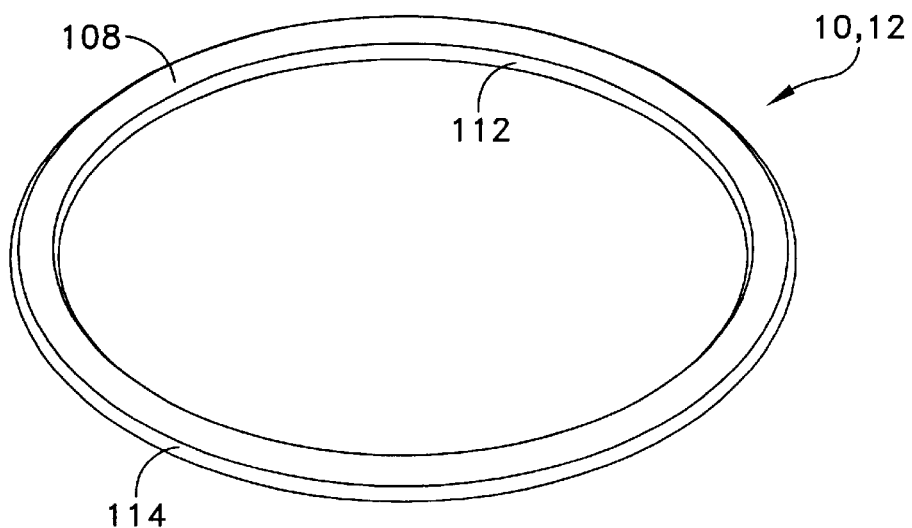
FIG. 52
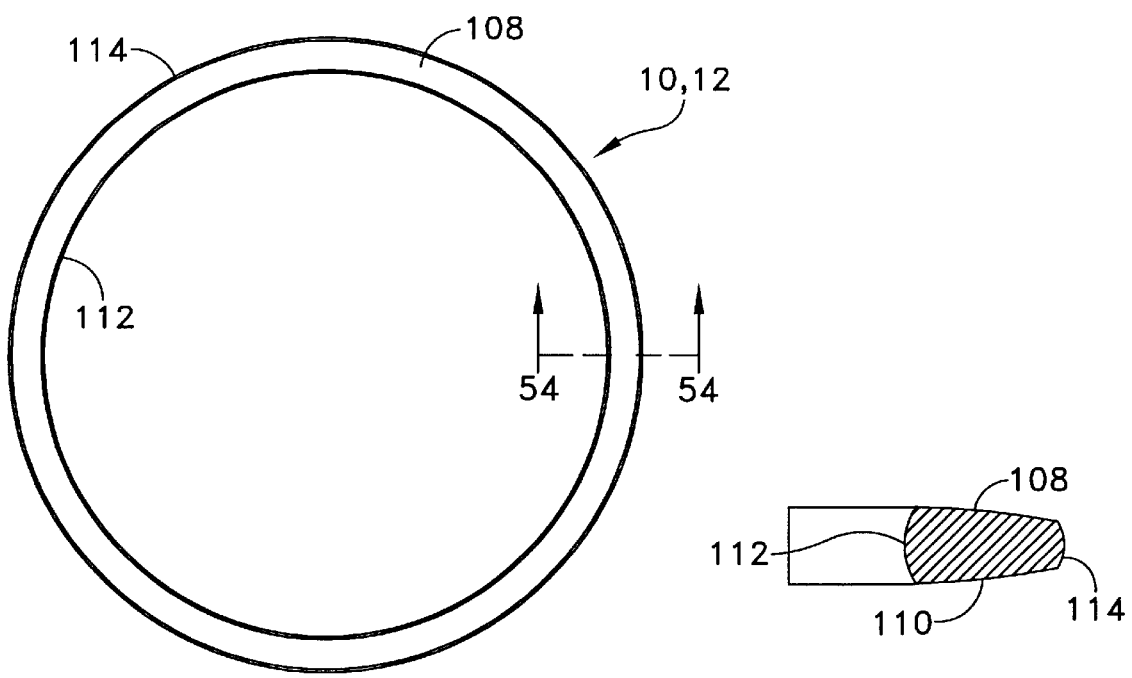
FIG. 53
FIG. 54

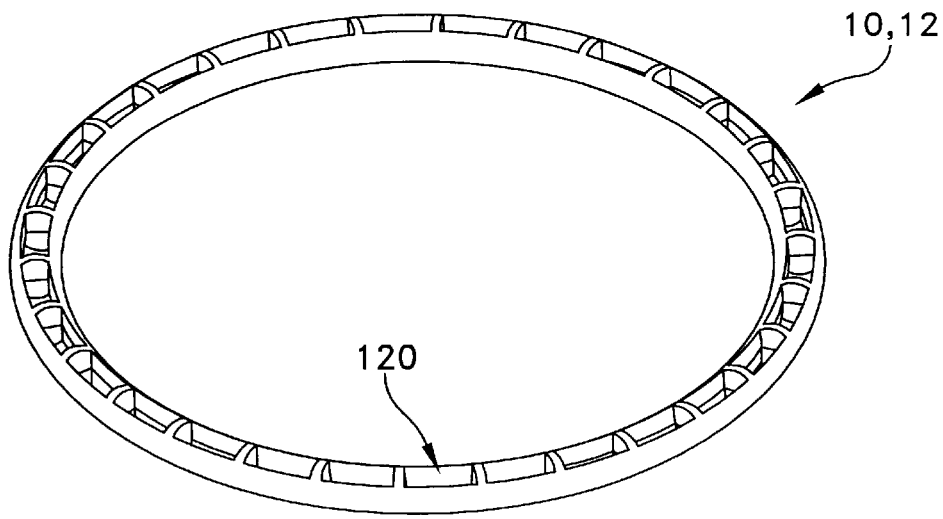
FIG. 58
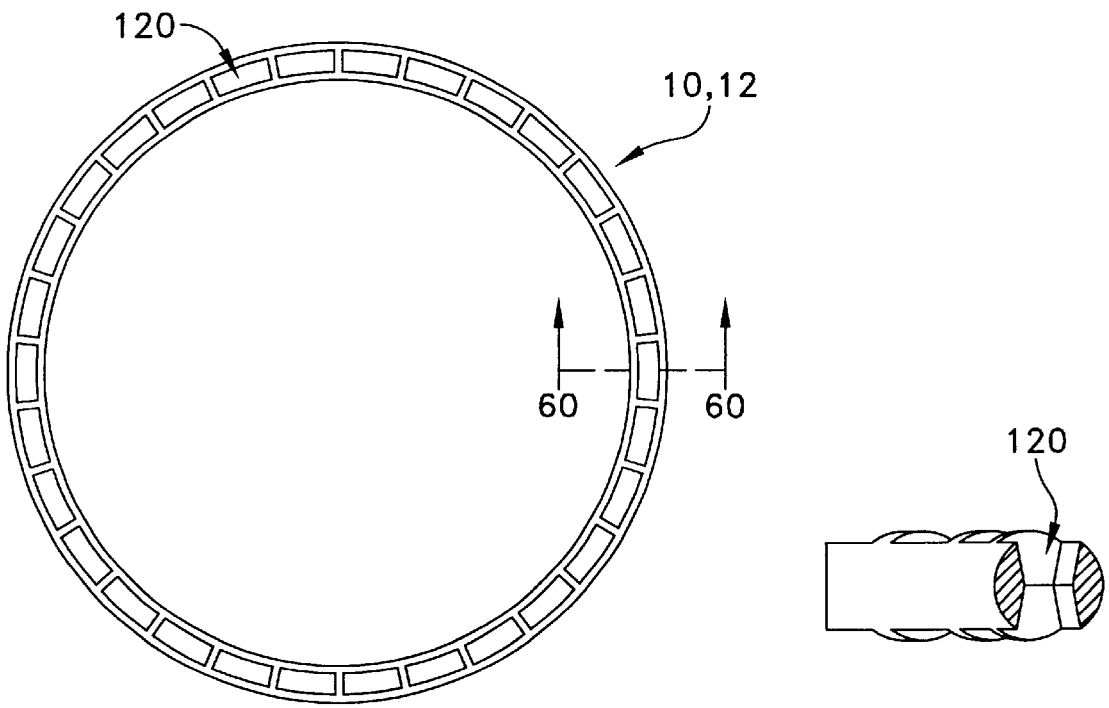
FIG. 59
FIG. 60

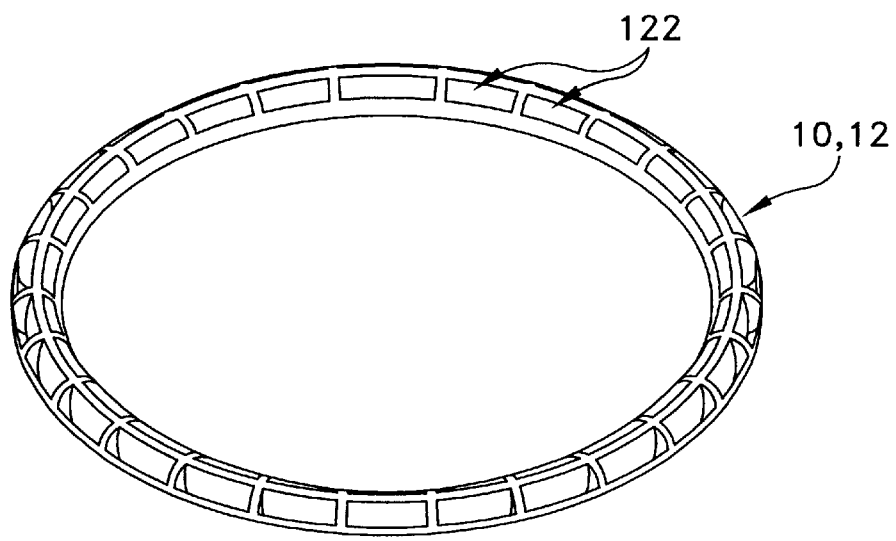
FIG. 61
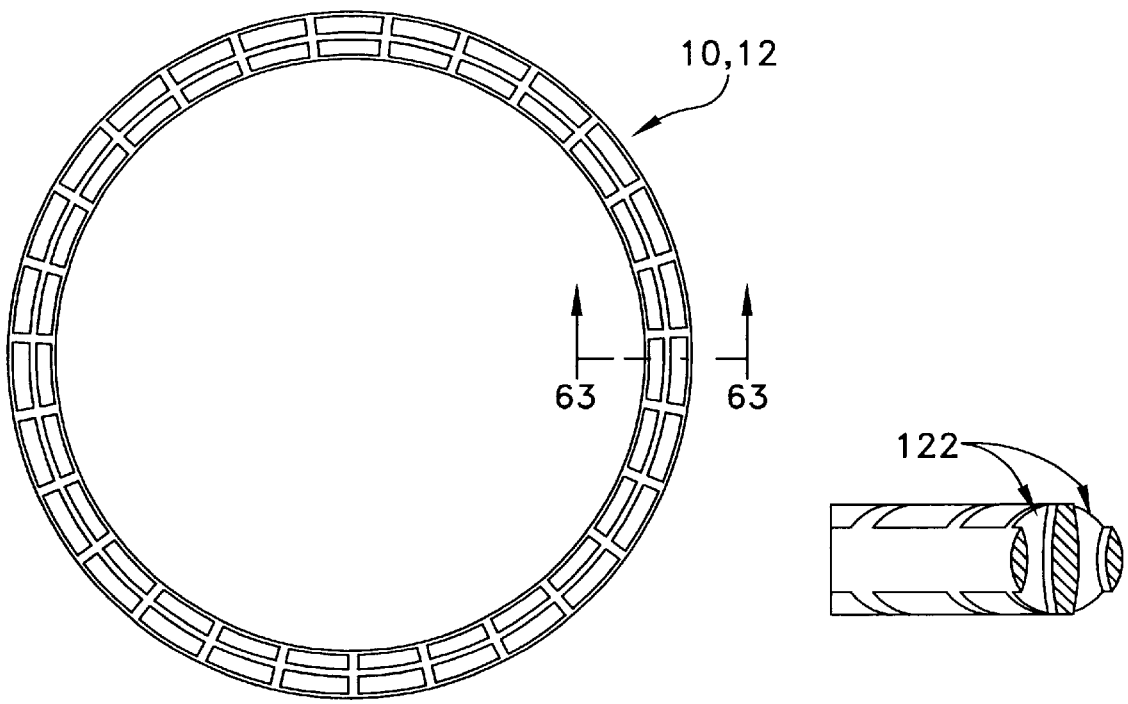
FIG. 62
FIG. 63

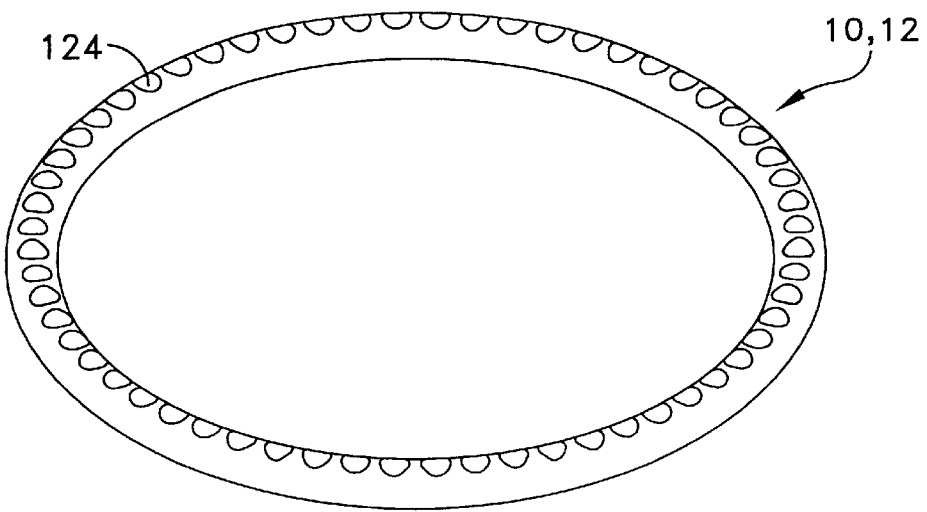
FIG. 64
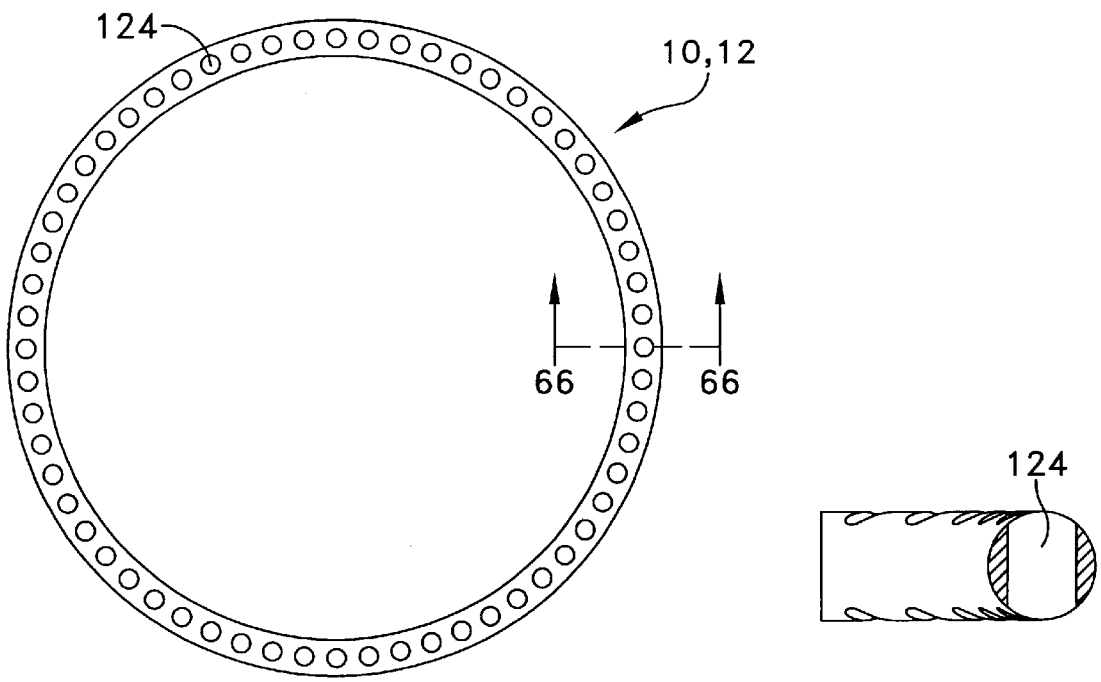
FIG. 65
FIG. 66

O-RING FOR INCREMENTALLY ADJUSTABLE INCISION LINER AND RETRACTOR

This application is a continuation application of U.S. application Ser. No. 09/970,416, filed on Oct. 3, 2001 now U.S. Pat No. 6,450,983.

FIELD OF THE INVENTION

The present invention relates generally to surgical wound protectors, and more particularly to an adjustable surgical wound protector for use in protecting incised cavity walls of various thicknesses from harmful contaminants during surgery.

BACKGROUND OF THE INVENTION

The sides of a wound during surgery are inherently susceptible to bacterial infection if touched by contaminated substances such as diseased body parts and fluids as they pass through the wound. Therefore extreme care must be exercised to insure that the exposed sides of an incision are completely covered by a material impervious to solids and fluids containing bacteria and other contaminants before surgery proceeds.

Various techniques have been used to insulate any incised tissue from exposure. One form of protection for relatively large incisions typically employs soft cotton sponges held against the sides of the wound by metal retractors to minimize contamination as well as to give the surgeon better access into the operating site. Another form of wound protector, particularly suitable for surgery, is disclosed in U.S. Pat. No. 3,347,227 to Harrower. Harrower discloses a surgical incision protector consisting of a pair of flexible rings joined by a thin, tubular-shaped sheet of flexible material. Harrower's rings have sufficient preforming to give a generally oval shape, be resilient and flexible, and so as to be easily flexed for insertion through a wound opening. The thin sheet is preferably made of plastic and must be impermeable to fluids and bacteria, physiologically inert, unaffected by autoclaving or sterilization, free of electrostatic hazard, resistant to melting, non-flammable, and somewhat elastic. Each of Harrower's flexible rings has a substantially circular cross-section. Harrower's incision protector is assembled by securing each end of the tubular sheet of flexible material to a ring, so that each ring is positioned at an end of the thin sheet of tubular material. In use, one ring is squeezed into an oblong shape, inserted through the peritoneum, and allowed to expand to the preformed shape over the inside edge of the wound. The other ring overlaps the outside edge causing the sleeve to stretch into contiguous contact with the entire surface of the sides and inner and outer edges of the wound. To obtain a form-fitting contiguous contact with the sides of the wound, the circumference of both rings in their preformed shape are slightly larger than that of the incision, and the extended length of the sleeve between the rings is slightly greater than that of the wall thickness. To accommodate variations in wound size, Harrower's wound protectors are manufactured in numerous combinations and permutations of both circumference and length.

U.S. Pat. No. 3,347,226 to Harrower describes an adjustable wound protector which reduces, to a degree, the number of sizes required. It requires a number of predetermined lengths similar to U.S. Pat. No. 3,347,227, except the circumference of the wound protector is adjustable, before being installed in the wound, by the rings having telescoping ends, and the side of the sleeve having overlapping lengthwise edges. Any overlapping excess may be cut off. The rings have a maximum adjustable circumference slightly larger than that of the largest incision anticipated so that they are sure to overlap the inner and outer edges of the wound. However, a sleeve length must be selected which will closely conform to the wall thickness at the wound.

U.S. Pat. No. 5,524,644, issued to Crook discloses an incrementally adjustable apparatus for protecting an incised wound from exposure to bacterial and other harmful contaminants. Crook provides a pair of resilient O-rings that are connected to opposite ends of an impermeable pliable sleeve. One of the O-rings is formed to engage the inner edge of the wound with a portion of the sleeve which is capable of being rolled onto the other ring to draw the remaining sleeve portion contiguous with the sides of the wound. Significantly, Crook relies upon flat surfaces on the rolled ring, that form an oblate cross-section, to provide a gripping surface to turn the ring about its annular axis.

SUMMARY OF THE INVENTION

In one preferred embodiment, an O-ring is provided for use in an adjustable surgical wound protector comprising a solid cross-section including a cross-sectional center that is spaced from a central longitudinal axis and a resilient configuration for squeezing into an oblong shape that is insertable into a surgical incision. At least one recess is defined in the O-ring that is selectively sized and shaped to enable a snap-action rolling of the O-ring about the cross-sectional center in predetermined increments. The recess may comprise various cross-sectional shapes, such as, at least one circumferential groove, a plurality of circumferentially positioned recesses, or be shaped such that the O-ring comprises a cruciform cross-section.

In one preferred embodiment of the invention, an O-ring is provided for use in an adjustable surgical wound protector that comprises a circular torus having a solid cross-section including a cross-sectional center that is radially equidistant from a central longitudinal axis. This O-ring also comprises a resilient configuration that is suitable for squeezing into an oblong shape that is insertable into a surgical incision. Advantageously, two recesses are formed in the O-ring that are selectively sized and shaped to enable a snap-action rolling of the O-ring about the cross-sectional center in predetermined increments. The circular cross-section of the O-rings preferably comprises four quadrants, with the material defining two diagonally opposed quadrants being removed, leaving two diagonally opposed recesses. The solid portion of each O-ring defines a first solid quadrant and a diagonally opposed second solid quadrant, with the first solid quadrant including a curved outer surface, a curved annular surface, and a sinusoidal surface, and the second solid quadrant also including a curved outer surface, a curved annular surface, and a sinusoidal surface. The first and second curved annular surfaces are preferably disposed at substantially the same radial distance from the central longitudinal axis, and are vertically oriented so as to be substantially parallel with the central longitudinal axis. The sinusoidal surfaces extend transversely relative to the central longitudinal axis.

An improved adjustable surgical wound protector is also provided that comprises an elongate open-ended tube formed of a pliable material that is impervious to solid and fluid contaminants for inserting lengthwise into a surgical incision. Two O-rings are one each secured around the open ends of the tube. The O-rings have a resilient configuration for overlapping the inner edge of the wound and for squeezing into an oblong shape that is insertable with a lengthwise portion of the sleeve adjacent to one of the O-rings in the surgical incision. Advantageously, at least one of the O-rings comprises at least one recess for enabling selected snap-action rolling of the at least one O-ring for rolling the remaining lengthwise portion of the sleeve on itself about the O-ring to shorten the sleeve in predetermined increments and to resist subsequent lengthening, whereby the sleeve length can be adjusted before or after placement in the wound.

BRIEF DESCRIPTION OF THE DRAWINGS

These and other features and advantages of the present invention will be more fully disclosed in, or rendered obvious by, the following detailed description of the preferred embodiment of the invention, which is to be considered together with the accompanying drawings wherein like numbers refer to like parts and further wherein:

FIGS. 6–9 illustrate in sequence, the operation of the incrementally adjustable surgical wound protector shown in FIG. 1;

FIG. 22 is a perspective view of yet a further alternative embodiment of O-ring;

FIG. 23 is a front elevational view of the O-ring shown in FIG. 22;

FIG. 24 is a cross-sectional view, as taken along lines 24—24 in FIG. 23;

FIG. 25 is a perspective view of yet a further alternative embodiment of O-ring;

FIG. 26 is a front elevational view of the O-ring shown in FIG. 25;

FIG. 27 is a cross-sectional view, as taken along lines 27—27 in FIG. 26;

FIG. 28 is a perspective view of yet a further alternative embodiment of O-ring;

FIG. 29 is a front elevational view of the O-ring shown in FIG. 28;

FIG. 30 is a cross-sectional view, as taken along lines 30—30 in FIG. 29;

FIG. 31 is a perspective view of yet a further alternative embodiment of O-ring;

FIG. 32 is a front elevational view of the O-ring shown in FIG. 31;

FIG. 33 is a cross-sectional view, as taken along lines 33—33 in FIG. 32

FIG. 40 is a perspective view of yet a further alternative embodiment of O-ring;

FIG. 41 is a front elevational view of the O-ring shown in FIG. 40;

FIG. 42 is a cross-sectional view, as taken along lines 42—42 in FIG. 41;

FIG. 43 is a perspective view of yet a further alternative embodiment of O-ring;

FIG. 44 is a front elevational view of the O-ring shown in FIG. 43;

FIG. 45 is a cross-sectional view, as taken along lines 45—45 in FIG. 44;

FIG. 46 is a perspective view of yet a further alternative embodiment of O-ring;

FIG. 47 is a front elevational view of the O-ring shown in FIG. 46;

FIG. 48 is a cross-sectional view, as taken along lines 48—48 in FIG. 47;

FIG. 49 is a perspective view of yet a further alternative embodiment of O-ring;

FIG. 50 is a front elevational view of the O-ring shown in FIG. 49;

FIG. 51 is a cross-sectional view, as taken along lines 51—51 in FIG. 50;

FIG. 52 is a perspective view of yet a further alternative embodiment of O-ring;

FIG. 53 is a front elevational view of the O-ring shown in FIG. 52;

FIG. 54 is a cross-sectional view, as taken along lines 54—54 in FIG. 53;

FIG. 58 is a perspective view of yet a further alternative embodiment of O-ring;

FIG. 59 is a front elevational view of the O-ring shown in FIG. 58;

FIG. 60 is a cross-sectional view, as taken along lines 60—60 in FIG. 59;

FIG. 61 is a perspective view of yet a further alternative embodiment of O-ring;

FIG. 62 is a front elevational view of the O-ring shown in FIG. 61;

FIG. 63 is a cross-sectional view, as taken along lines 63—63 in FIG. 62;

FIG. 64 is a perspective view of yet a further alternative embodiment of O-ring;

FIG. 65 is a front elevational view of the O-ring shown in FIG. 64;

FIG. 66 is a cross-sectional view, as taken along lines 66—66 in FIG. 65;

DETAILED DESCRIPTION OF THE PREFERRED EMBODIMENT

Figure 1:
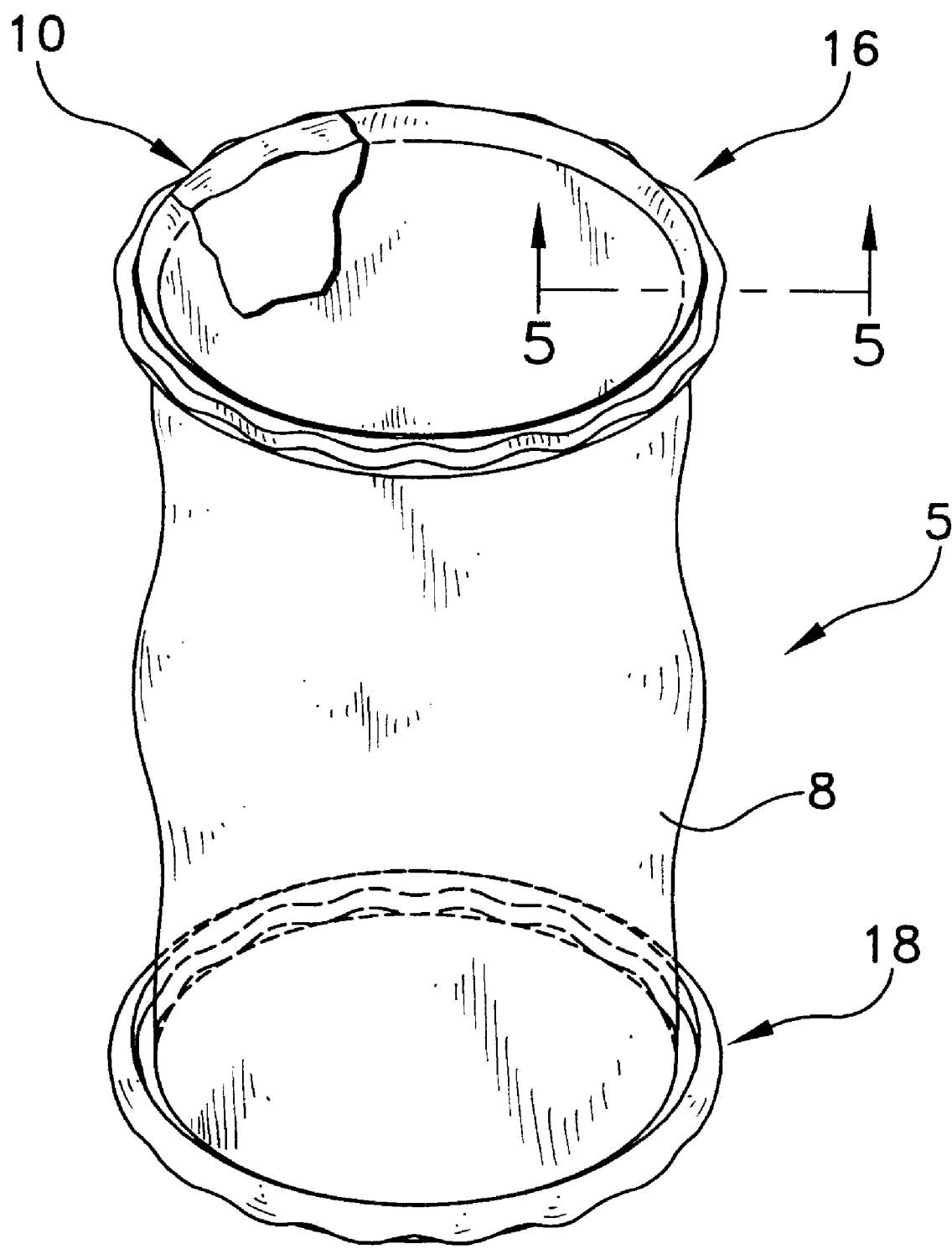
FIG. 1 is a perspective, partially broken away view of an incrementally adjustable surgical wound protector formed in accordance with the present invention.

This description of preferred embodiments is intended to be read in connection with the accompanying drawings, which are to be considered part of the entire written description of this invention. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship. In the claims, means-plus-function clauses are intended to cover the structures described herein as performing the recited function, including not only structural equivalents but also equivalent structures.

Referring to FIG. 1, an incrementally adjustable surgical wound protector 5 comprises a thin flexible sleeve 8 positioned between a first O-ring 10 and a second O-ring 12. Sleeve 8 comprises a tube having a uniform circumference along its length, an upper end edge 16, and a lower end edge 18. Upper end edge 16 of sleeve 8 is fastened or bonded to a surface portion of first O-ring by sealing, e.g., thermally, ultrasonically or, with proper pretreatment, adhesives, but without (i) the portion of sleeve 8 adjacent to upper end edge 16 being wrapped around the circumference of first O-ring 10, or (ii) overlapped upon itself. Likewise, lower end edge 18 of sleeve 8 is fastened or bonded to a surface portion of O-ring 12 by sealing, e.g., thermally, ultrasonically or, with proper pretreatment, adhesives, but without (i) the portion of sleeve 8 adjacent to lower end edge 18 being wrapped around the circumference of O-ring 12, or (ii) overlapped upon itself (FIGS. 5–9). Sleeve 8 may also be attached to O-rings 10,12 by adhesive, but with less than satisfactory results.

Sleeve 8 is preferably formed from a material that is impervious to solids and/or fluids containing bacteria and other harmful contaminants, e.g., a polymer or elastomeric material of the type known in the art. The materials and dimensions of wound protector 5 are selected to ensure stability of the wound protector when installed. A preferred polymer material suitable for sleeve 8 is a heat-sealable 2-mil aromatic polyether polyurethane film, such as the PT6100 series manufactured by Deerfield Urethane, Inc., under the tradename DUROFLEX, that may be produced in seamless tubular form or by a flat sheet in a cylindrical form with the meeting margins along the side overlapped and sealed. Other materials that may be used with good effect include, polyolefins and other like plastomers and elastomers that are suitable for use in medical applications. A nominal sleeve length suitable for surgery is typically from about 100 to about 200 mm. Sleeve diameters will vary according to the length of the surgical incision.

First O-ring 10 and second O-ring 12 each are formed so as to engage the inner edge of a surgical incision, with a portion of sleeve 8 above the incision and capable of being incrementally rolled toward the other O-ring to draw the remaining portion of sleeve 8 contiguous with the sides of the incision. O-rings 10 and 12 are preferably formed from an elastomeric medical grade material of sufficient hardness to retain O-rings 10 and 12 expanded in place around the inner and outer edges of the surgical incision. The material must be compliant enough to allow O-ring 10 or 12 to be turned by the fingers over 180 degrees about its center. For this purpose, urethane is a preferred elastomeric material. O-rings 10,12 may be formed from other resilient materials, such as medical grade, polyvinylchloride, silicon, natural rubber, or other elastomeric or rubber-like materials, with good effect.

Referring to FIGS. 1–5, O-rings 10,12 preferably comprise a circular torus, i.e., a solid formed by the rotation of a circle about an axis that lies in the plane of the circle, but without cutting the circle. O-rings 10,12 are formed from a solid, initially circular cross-section torus having a cross-sectional center 20 that is radially equidistant from a central longitudinal axis 24 of the O-ring. The circular cross-section of each O-ring 10,12 may be divided into four quadrants (FIGS. 3, and 5–9). Material defining two diagonally opposed quadrants is removed, leaving two diagonally opposed recesses 26 and 28 (best shown in FIG. 3).

Figure 2:
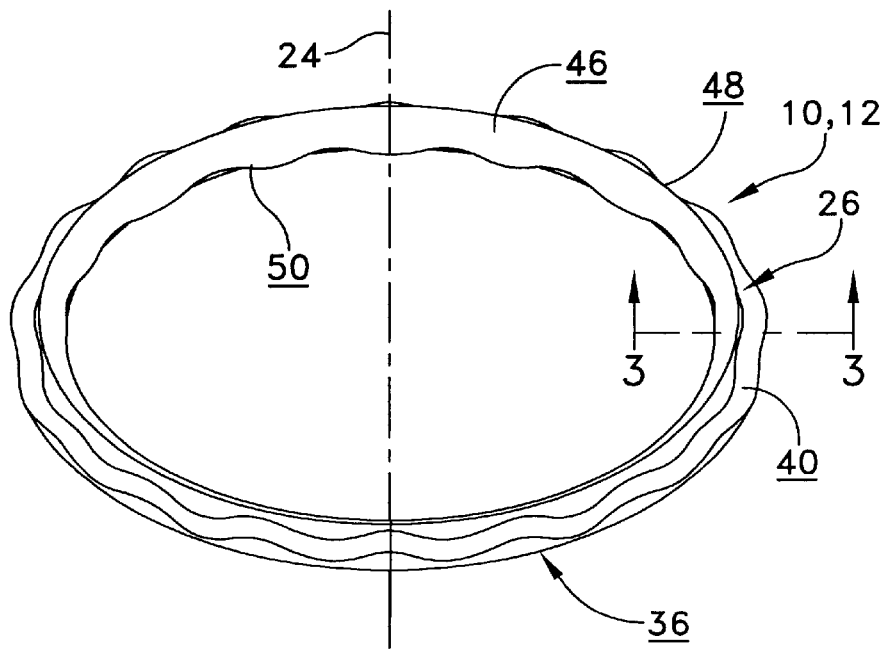
FIG. 2 is a perspective view of an O-ring formed in accordance with a preferred embodiment of the present invention.
Figure 3:
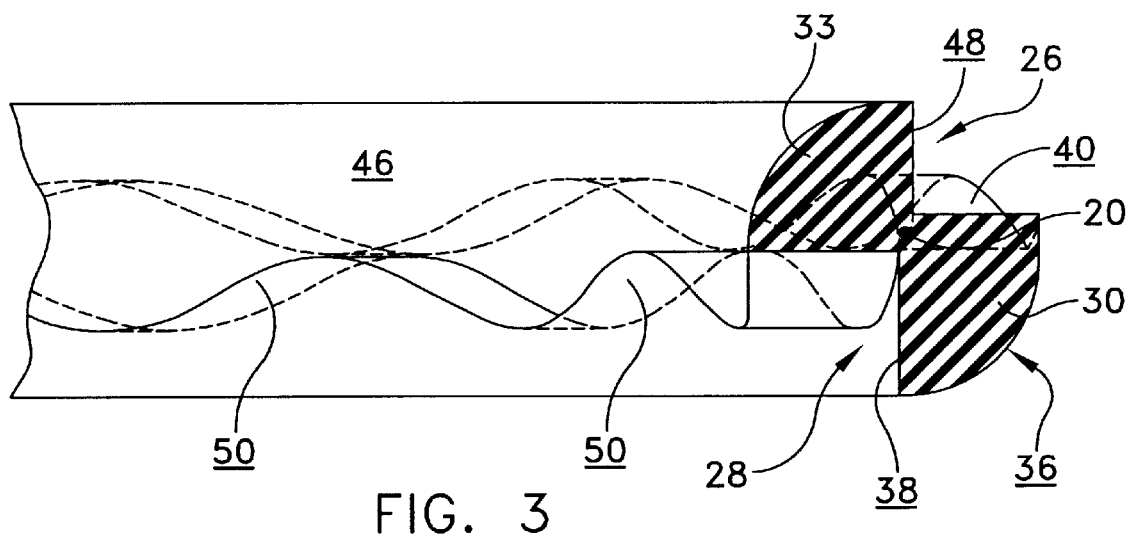
FIG. 3 is a cross-sectional view of the O-ring shown in FIG. 2, as taken along lines 3—3 in FIG. 2, and including a portion of the interior side surface of the O-ring.
Figure 4:
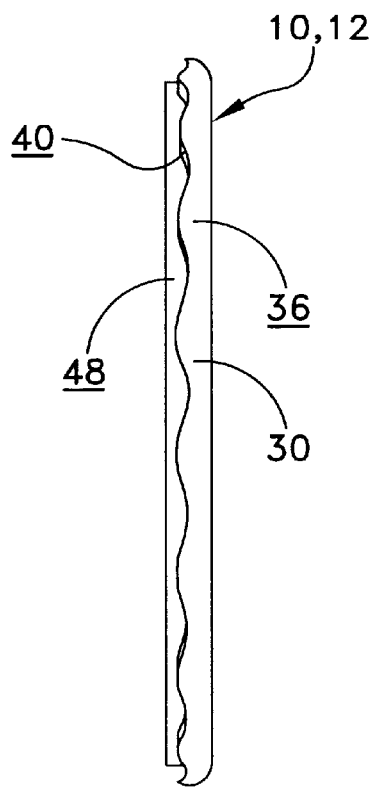
FIG. 4 is a side elevational view of the O-ring shown in FIG. 2.

The solid portion of O-rings 10,12 that remains defines a first solid quadrant 30 and a diagonally opposed, second solid quadrant 33. First solid quadrant 30 includes a curved outer surface 36, a curved annular surface 38, and a sinusoidal surface 40. Second solid quadrant 33 includes a curved outer surface 46, a curved annular surface 48, and a sinusoidal surface 50. Curved annular surfaces 38,48 are at substantially the same radial distance from central longitudinal axis 24, and are vertically oriented so as to be substantially parallel and substantially coaxial with central longitudinal axis 24. Sinusoidal surfaces 40,50 extend transversely relative to the central longitudinal axis 24 of O-rings 10,12 (FIGS. 2 and 3).

Of course, it will be understood that the term "O-ring" is not limited to circular structures or classic toroidal shapes, but also includes structures that are not circular, e.g., rectilinear, oval/elliptical, hexagonal, octagonal, etc., as long as such rings comprise a resilient configuration capable of being squeezed into an oblong shape that is suitable for insertion into a surgical incision.

Figure 5:
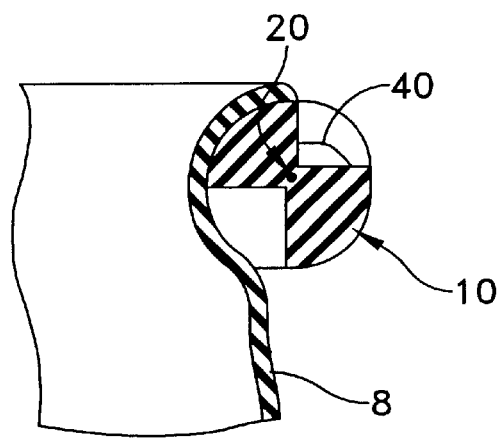
FIG. 5 is a broken away, cross-sectional view of the incrementally adjustable surgical wound protector shown in FIG. 1, as taken along lines 5—5 in FIG. 1, illustrating the interconnection between the O-ring and sleeve.
Figure 10:
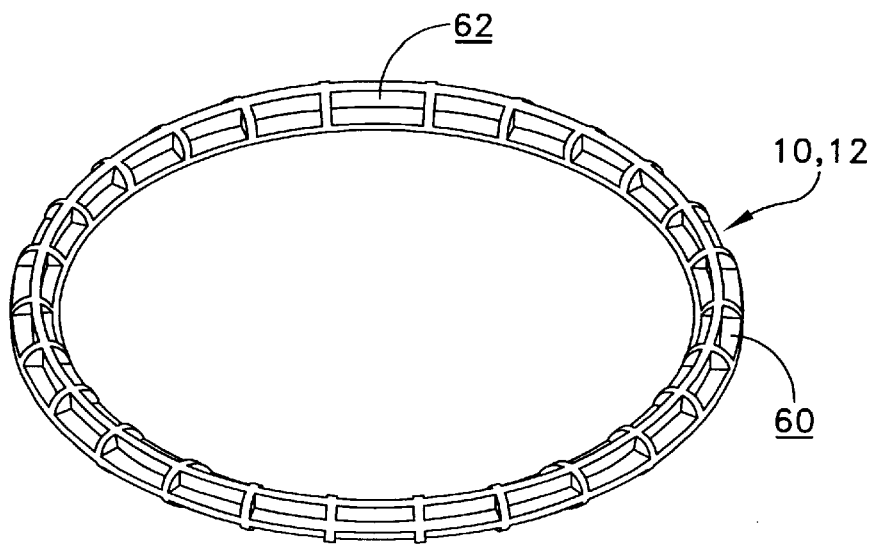
FIG. 10 is a perspective view of one alternative embodiment of O-ring.
Figure 11:
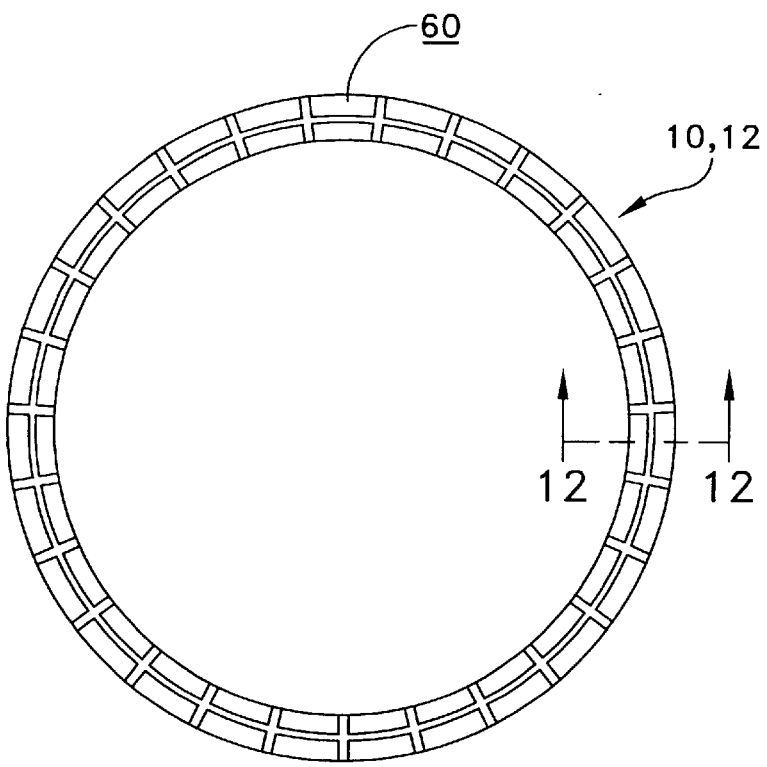
FIG. 11 is a side elevational view of the O-ring shown in FIG. 10.

By way of example, a urethane O-ring 10,12 for use with a sleeve having a diameter of about 109 mm, has a diameter of about 7.9 mm, with a radial depth of diagonally opposed recesses 26 and 28 of approximately 4.0 mm. Of course, the sizes of the O-rings and sleeves will vary according to incision size and peritoneum wall thickness. The personal preference of the surgeon will also affect the choice of both O-ring and sleeve size for a particular surgical procedure. Each end of sleeve 8 is sealingly fastened or bonded around an O-ring 10,12, e.g., to a curved outer surface 46, such that when the sleeve is fully extended, O-rings 10,12 are positioned in spaced-apart relation to one another (FIGS. 1 and 5).

The cross-sectional shape of O-rings 10,12 provides stability in a plane perpendicular to central longitudinal axis 24, and provides an over-center "snap-action" or "snap-roll" when O-ring 10, 12 is rolled about itself and sleeve 8, thereby providing incremental shortening in predetermined increments and resistance to lengthening after shortening. More particularly, by strategically removing portions of O-rings 10,12 so as to form recesses 26,28, the rate of twist necessary to create the over-center "snap-action" can be gauged and set. Typically, about 33% to about 70% of the mass of the O-ring must be either removed or redistributed in order to obtain a "snap-action" that is suitable for hand twisting. Thus numerous O-rings (FIGS. 12–39), having differing amounts, locations, and shapes of material removed from their cross-section may be used in connection with the present invention.

Figure 12:
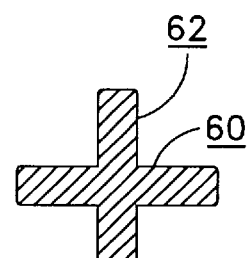
FIG. 12 is a cross-sectional view, taken along line 12—12 in FIG. 11.
Figure 12A:
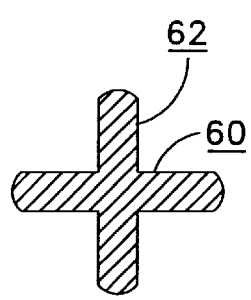
FIG. 12A is a cross-sectional view similar to that shown in FIG. 12, but illustrating an alternative cruciform cross-section having radiused end surfaces.
Figure 13:
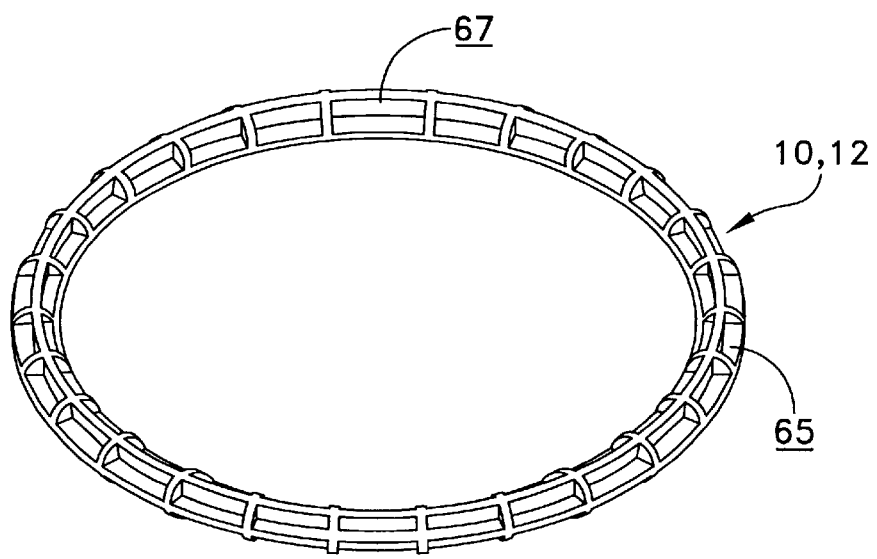
FIG. 13 is a perspective view of another embodiment of O-ring.
Figure 14:
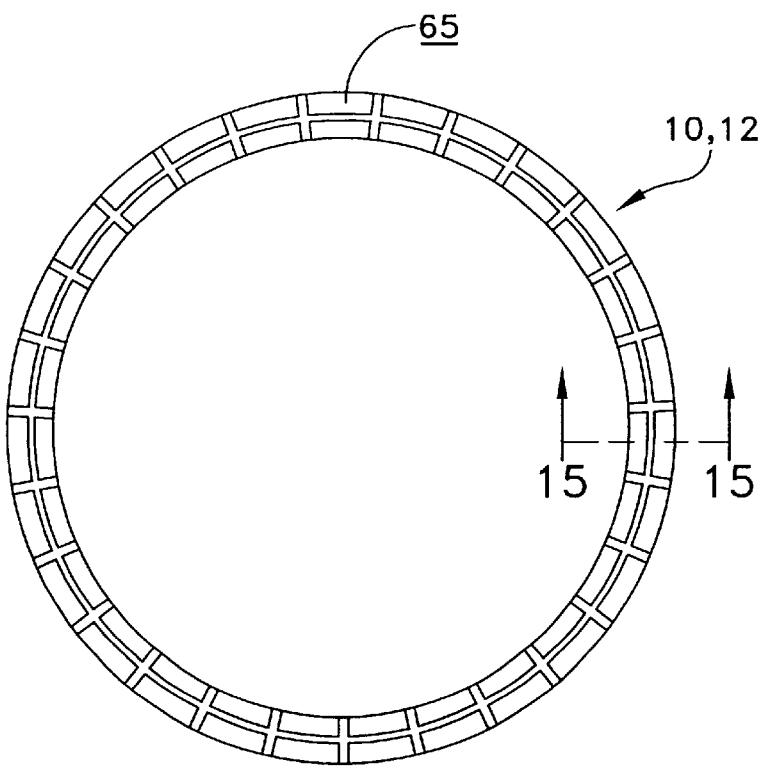
FIG. 14 is a side elevational view of the O-ring shown in FIG. 13.
Figure 15:
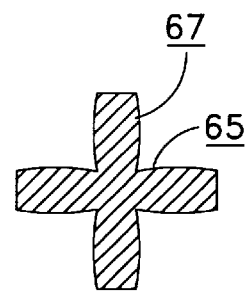
FIG. 15 is a cross-sectional view, as taken along lines 15—15 in FIG. 14, showing an alternative cruciform cross-section.
Figure 15A:
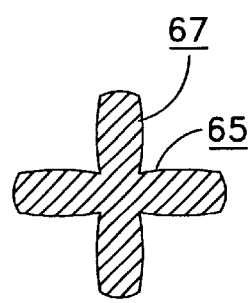
FIG. 15A is a cross-sectional view similar to that shown in FIG. 15, but illustrating an alternative cruciform cross-section having radiused end surfaces.

For example, and referring to FIGS. 10–15, rings 10,12 may comprise a cruciform cross-sectional profile. In this configuration, the cruciform shape of O-rings 10,12 provide stability in a plane perpendicular to central longitudinal axis 24 and also provide the over-center, "snap-action" when rolled about themselves and sleeve 8. The embodiment disclosed in FIGS. 10–12 include a cruciform cross-section having flat surfaces 60 and 62. While FIGS. 13–15 show a similar O-ring 10,12 having radiused surfaces 65 and 67. Of course, the end surfaces of the cruciform cross-section O-ring 10,12 may also have radiused end surfaces, as shown in FIGS. 12A and 15A.

Figure 16:
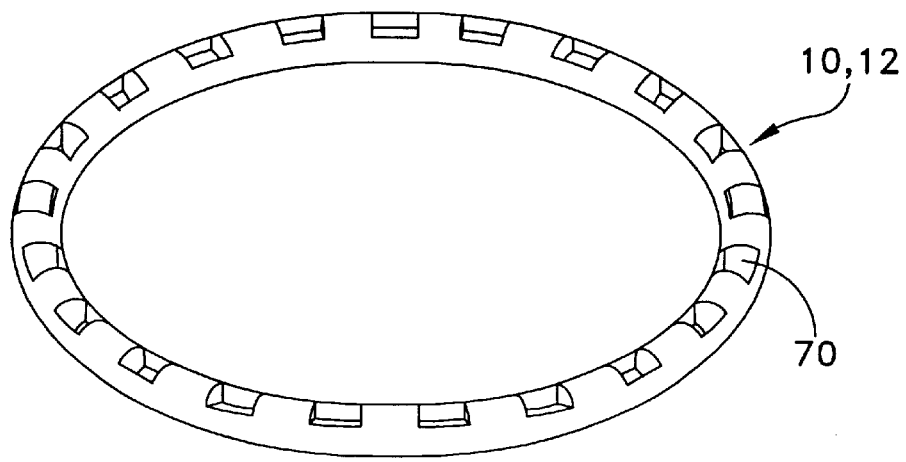
FIG. 16 is a perspective view of yet another alternative embodiment of O-ring.
Figure 17:
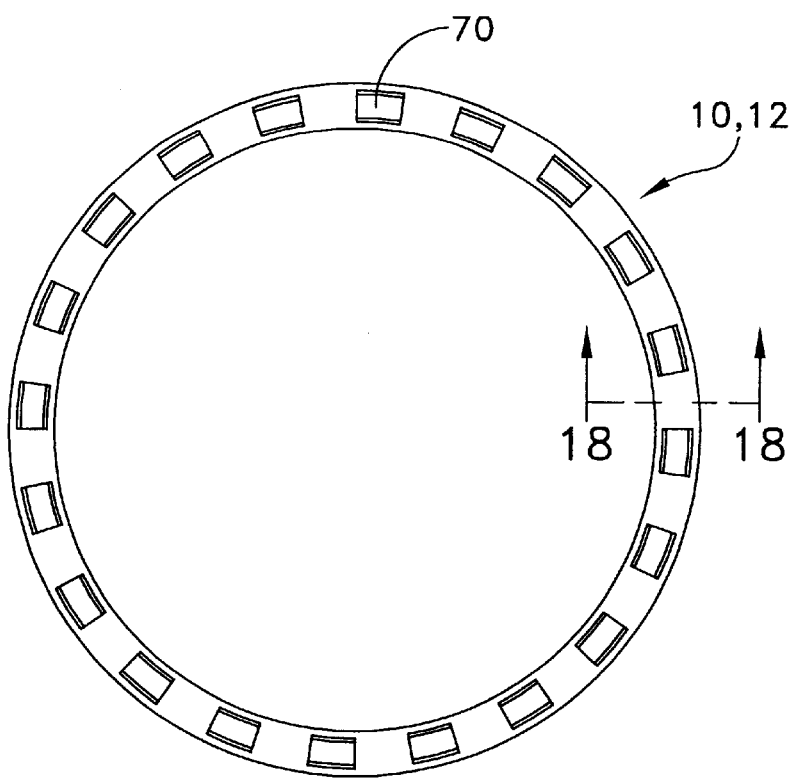
FIG. 17 is a side elevational view of the O-ring shown in FIG. 16.
Figure 18:
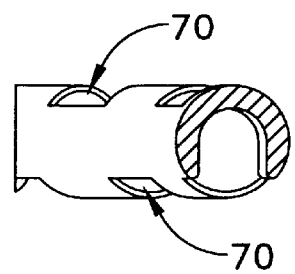
FIG. 18 is a cross-sectional view, as taken along line 18—18 in FIG. 17, showing an embodiment of recess used in connection with the present invention.
Figure 19:
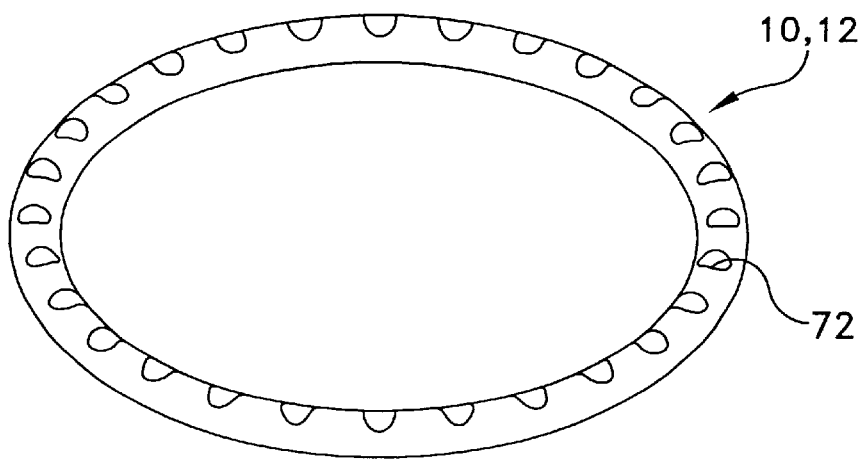
FIG. 19 is a perspective view of a further alternative embodiment of O-ring.
Figure 20:
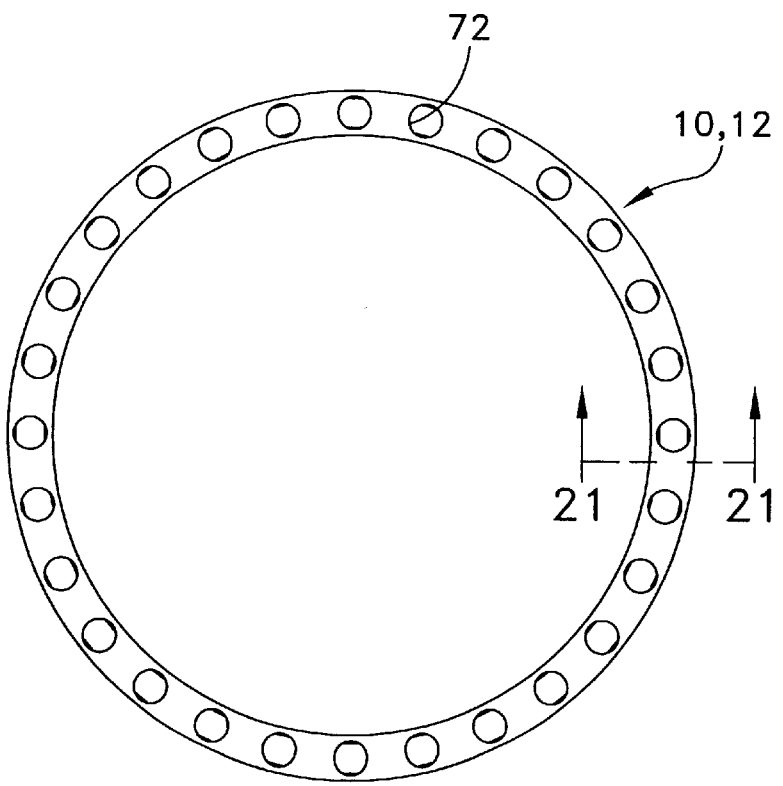
FIG. 20 is a side elevational view of the O-ring shown in FIG. 19.
Figure 21:
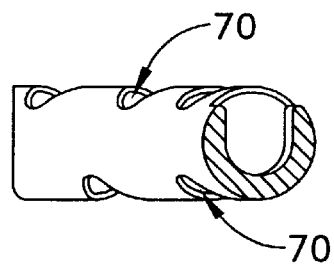
FIG. 21 is a cross-sectional view, as taken along the line 21—21 in FIG. 20.
Figure 34:
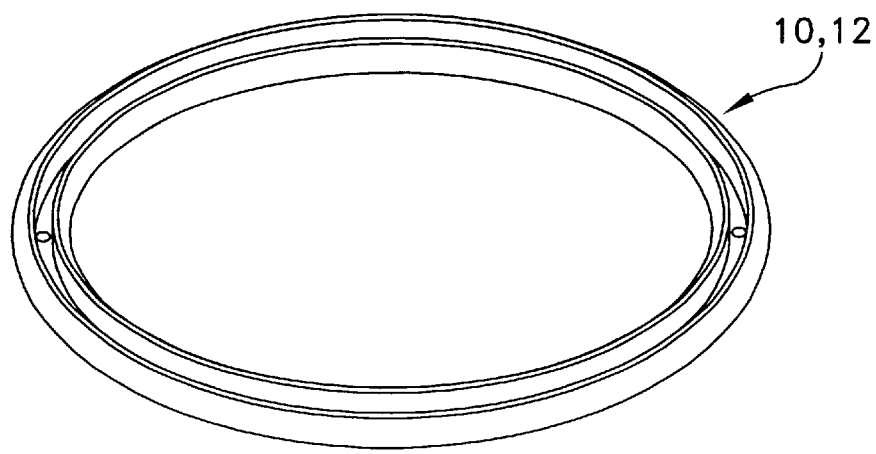
FIG. 34 is a perspective view of yet a further alternative embodiment of O-ring.
Figure 35:
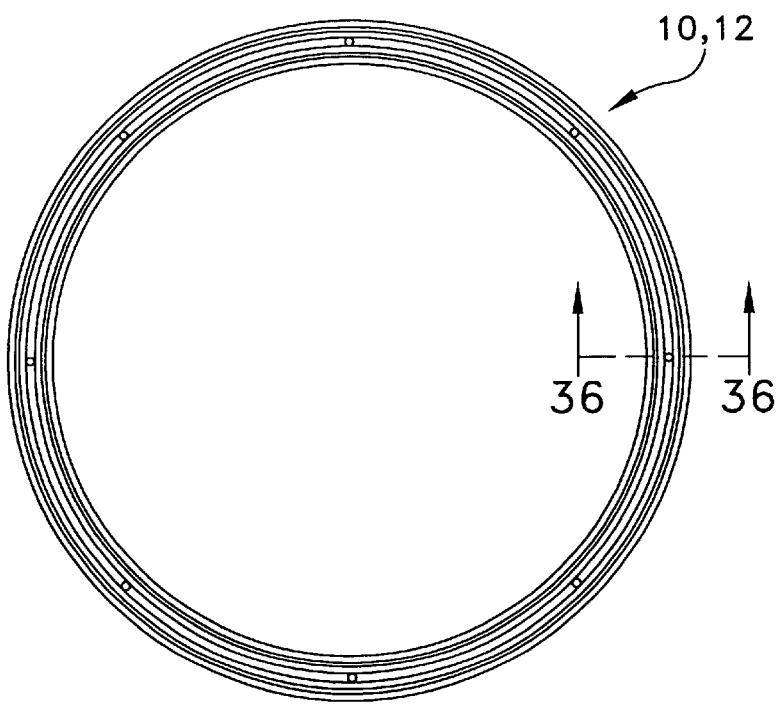
FIG. 35 is a front elevational view of the O-ring shown in FIG. 34.
Figure 36:
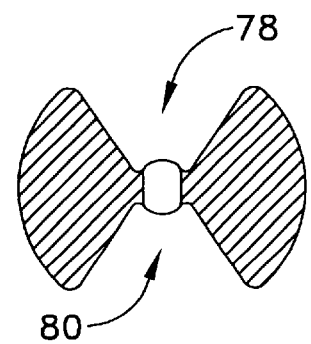
FIG. 36 is a cross-sectional view, as taken along lines 36—36 in FIG. 35.

Referring to FIGS. 16–33, O-rings 10,12 may also include a plurality of recesses defined into a portion of the ring. More particularly, a plurality of recesses 70 are defined radially inwardly into O-ring 10,12, i.e., toward cross-sectional center 20, from diametrically opposed positions along the circumference of the O-ring. In this way, recesses 70 extend into O-ring 10,12 from each side in an alternating pattern. FIGS. 16–18 illustrate a rectilinearly shaped plurality of alternating recesses 70, while FIGS. 19–21 illustrate a plurality of round recesses 72 and FIGS. 22–24 illustrate a plurality of round, shallow recesses 72a disposed on both sides of O-ring 10,12.

Referring to FIGS. 25–33, a sinusoidally defined recess 72b may be employed with the present invention. FIGS. 25–27 illustrate such a sinusoidal recess 72b disposed on an inner circumferential surface of O-ring 10,12, while FIGS. 28–30 illustrate such a sinusoidal recess 72b disposed on an outer circumferential surface of O-ring 10,12. FIGS. 31–33 illustrate a pair of sinusoidal recesses 72b positioned in diametrically opposed relation to one another on O-ring 10,12. In each of the foregoing cases, the removal of material from O-ring 10, 12 to define recesses 70, 72, or 72b provides stability in a plane perpendicular to central longitudinal axis 24, and provides an over-center "snap-action" when the O-ring is rolled about itself and sleeve 8.

Figure 37:
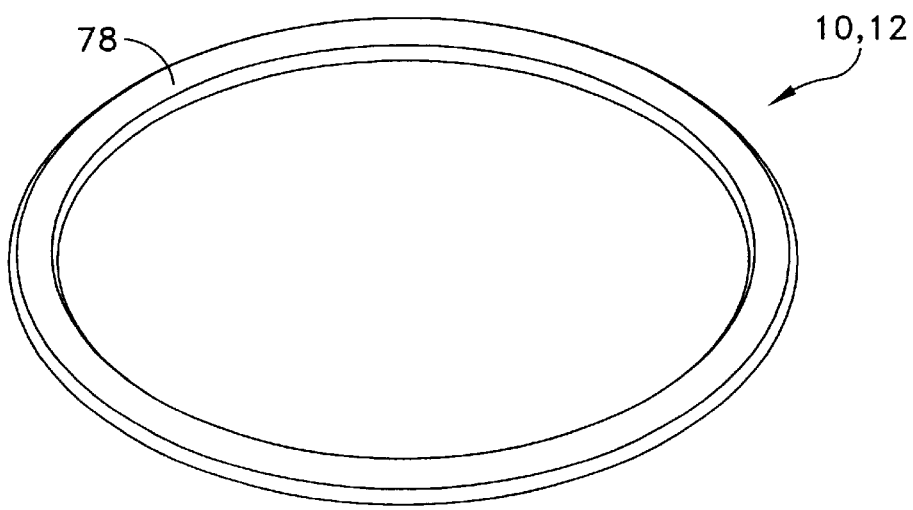
FIG. 37 is a perspective view of yet a further alternative embodiment of O-ring.
Figure 38:
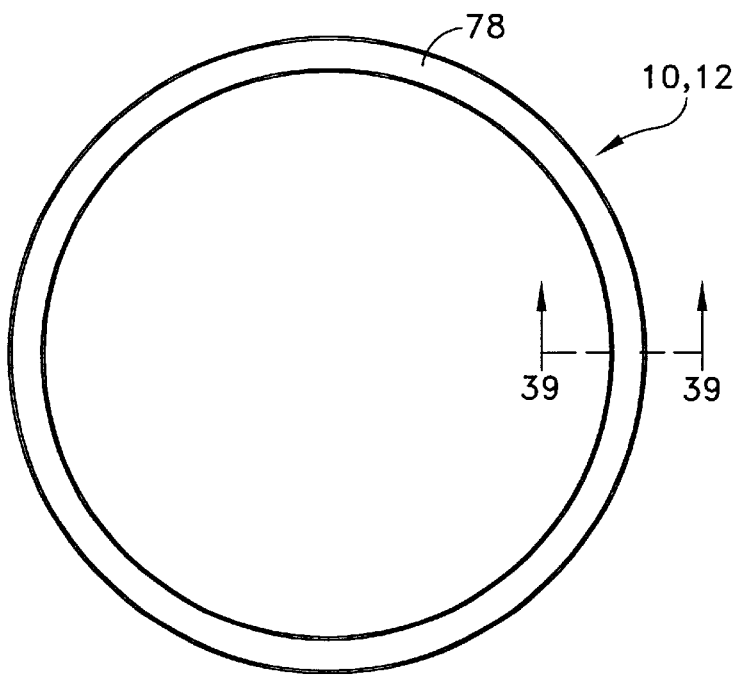
FIG. 38 is a front elevational view of the O-ring shown in FIG. 37.
Figure 39:
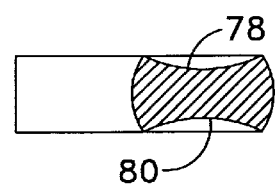
FIG. 39 is a cross-sectional view, as taken along lines 39—39 in FIG. 38.

Referring to FIGS. 34–42, O-rings 10,12 may also have a continuous recess formed in diametrically opposed portions of O-ring 10,12. More particularly, a top recess 78 and a bottom recess 80 may be formed in O-ring 10,12 so as to yield "a bow-tie" cross-sectional profile to O-ring 10, 12 (FIGS. 34–36) or may be formed so as to be shallow (FIGS. 37–39). The removal of material from O-ring 10, 12 from diametrically opposed portions in a continuous, or annular fashion, provides stability in a plane perpendicular to central longitudinal axis 24, and provides an over-center "snap-action" when the O-ring is rolled about itself and sleeve 8. A plurality of reinforcing ribs 82 may be formed within top recess 78 and/or bottom recess 80 so as to ease manufacture (FIGS. 40–42).

Referring to FIGS. 43–57, O-rings 10,12 may also be formed so as to have convex top and bottom walls 86,88, and substantially flat inner and outer, annular side walls 90, 92 (FIGS. 43–45) or convex top and bottom walls 86,88 and convex inner and outer, annular side walls 94,96 (FIGS. 46–48). The reduction of material from O-ring 10,12 coupled with the curvature of either the top and bottom walls 86,88 or the annular inner and outer side walls 94,96 provides stability in a plane perpendicular to central longitudinal axis 24, and provides an over-center "snap-action" when the O-ring is rolled about itself and sleeve 8.

Figure 55:
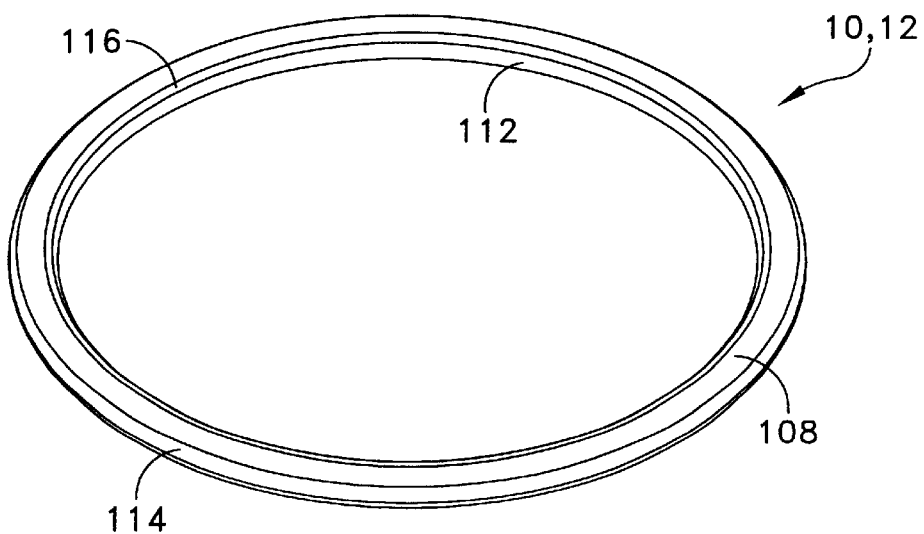
FIG. 55 is a perspective view of yet a further alternative embodiment of O-ring.
Figures 56, 57:
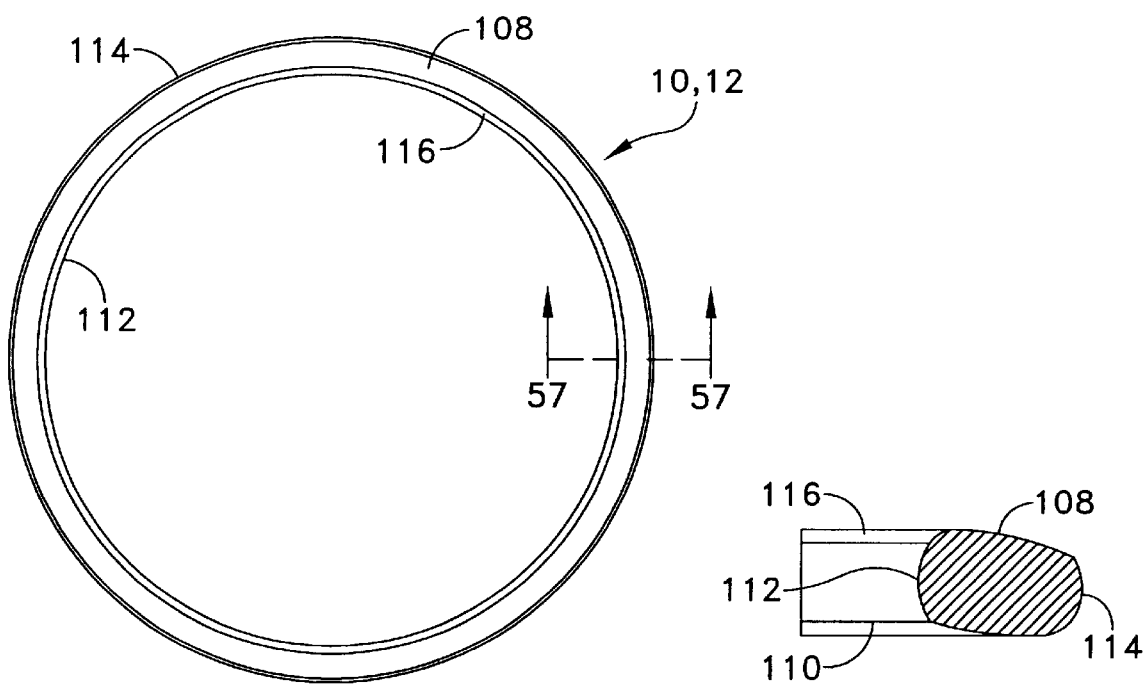
FIG. 56 is a front elevational view of the O-ring shown in FIG. 55.
FIG. 57 is a cross-sectional view, as taken along lines 57—57 in FIG. 56.

Additionally, O-ring 10,12 may also be formed so as to have nonparallel top and bottom walls 100,102, and convex inner and outer, annular side walls 104,106 (FIGS. 49–51). Alternatively, O-ring 10,12 may also be formed so as to have nonparallel, convex top and bottom walls 108,110, and convex inner and outer, annular side walls 112,114 (FIGS. 52–54). Also, an additional annular flat 116 may be included at the transition between convex inner and outer, annular side walls 112,114 and convex top and bottom walls 108,110 (FIGS. 55–57).

Referring to FIG. 58-, O-rings 10,12 may also include a plurality of through-holes 120 defined radially through O-ring 10,12, i.e., through cross-sectional center 20, from diametrically opposed positions along the circumference of the O-ring. FIGS. 58–63 illustrate a plurality of rectilinearly shaped through-holes 120, and double through-holes 122, respectively, while FIGS. 64–66 illustrate a plurality of round through-holes 124. In each case, the removal of material from O-ring 10, 12 to define through-holes 120, 122, or 124 provides stability in a plane perpendicular to central longitudinal axis 24, and provides an over-center "snap-action" when the O-ring is rolled about itself and sleeve 8.

Figure 67:
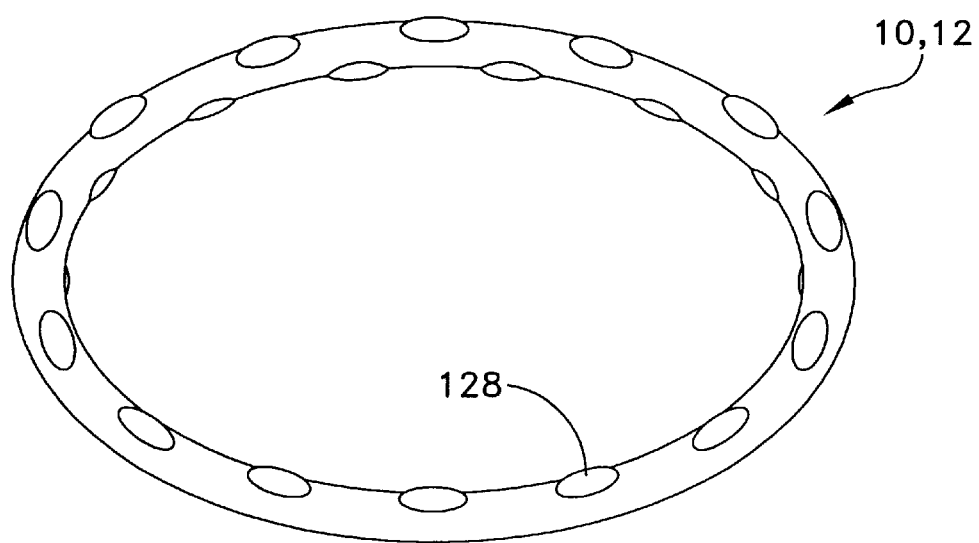
FIG. 67 is a perspective view of yet a further alternative embodiment of O-ring.
Figure 68:
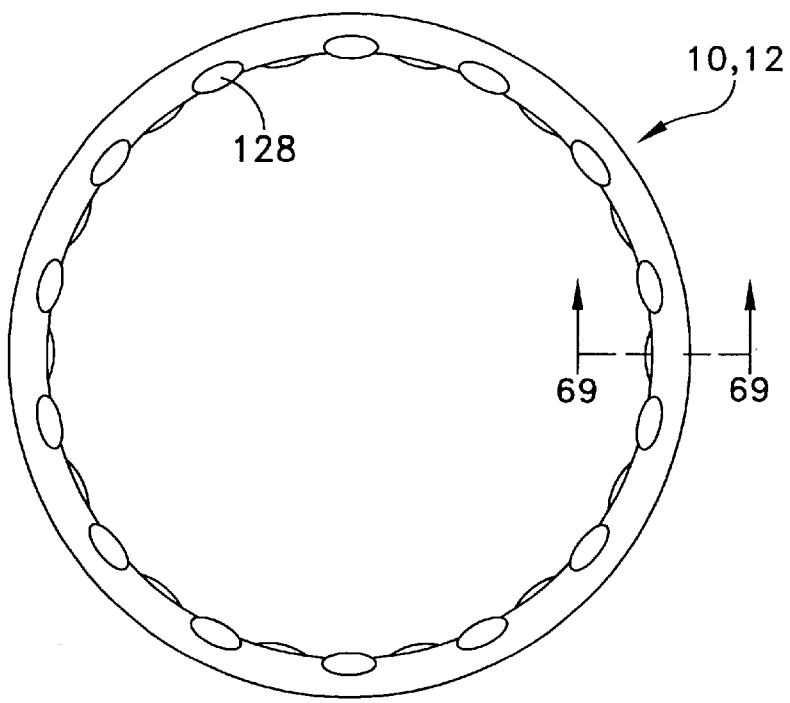
FIG. 68 is a front elevational view of the O-ring shown in FIG. 67.
Figure 69:
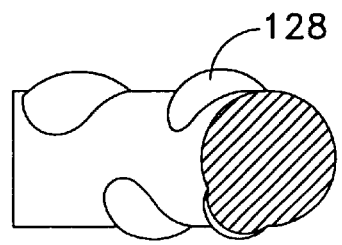
FIG. 69 is a cross-sectional view, as taken along lines 69—69 in FIG. 68.

Referring to FIGS. 67–69, in some instances, O-rings 10,12 may have additional material added to their circumference so as to form bulbous protrusions 128 over their outer surface, so as to redistribute the mass of the O-ring 10,12. This redistribution of mass and concomitant change in the moment of inertia of O-ring 10,12 also provides stability in a plane perpendicular to central longitudinal axis 24, and provides an over-center "snap-action" when the O-ring is rolled about itself and sleeve 8.

Referring again to FIGS. 6–9, when adjustable surgical wound protector 5 is to be used in an abdominal surgical procedure, the abdomen 55 is routinely prepared with antiseptics; the site for the incision is traced on abdomen 55 and covered with a surgical drape; and a muscle-split is made at the site through the peritoneum. One O-ring (identified by reference numeral 12 in FIGS. 6–9) is squeezed lengthwise and inserted into the surgical incision and through the peritoneum, where it is released and returns to its original circular shape. In this position, O-ring 12 is placed within the body cavity and O-ring 10 is positioned outside of the body cavity, with sleeve 8 extending through the body cavity. It will be understood that O-rings 10, 12 are completely interchangeable. Outer O-ring 10 is then gripped by the thumb and fingers and turned outwardly, in opposite directions, so as to roll sleeve 8 incrementally, i.e., so as to create repeated over-center "snap-rolls" of the O-ring. As a consequence, sleeve 8 is reeled onto outer O-ring 10 until outer O-ring 10 abuts the outer surface of abdomen 55. The portion of sleeve 8 that is in the incision, and between O-rings 10,12 is drawn into contiguous contact with the sides of the incision so as to provide a self-retaining protective barrier during surgery which is impervious to contaminating solids and fluids.

ADVANTAGES OF THE INVENTION

Numerous advantages are obtained by employing the present invention.

The present invention provides a relatively low cost surgical wound protector of simplified and selectively adjustable design which can be easily installed in a wound and adjusted in place to form fit a wide range of cavity wall thicknesses for protection against harmful contaminants.

Another advantage of the invention is the provision of an adjustable wound protector in which relatively few sizes are needed to form fit a wide range of incision sizes and cavity wall thicknesses.

Still another advantage of the invention is the provision of a surgical wound protector which can be adjusted after being inserted in a wound to obtain contiguous contact with the sides of the cavity wall.

A still further advantage of the invention is the provision of a single, easily manufactured O-ring design that provides for a "snap=action" when rolled in itself so as to reel a sleeve onto the O-ring after being inserted in an incision for securing the sleeve in contiguous contact with the sides of the incision.

It is to be understood that the present invention is by no means limited only to the particular constructions herein disclosed and shown in the drawings, but also comprises any modifications or equivalents within the scope of the claims.

What is claimed is:

1. An O-ring for use in an adjustable surgical wound protector, comprising:
    a circular torus having a circular cross-section comprising four quadrants wherein material defining two diagonally opposed quadrants is removed, leaving two diagonally opposed recesses and a solid cross-section including a cross-sectional center that is radially equidistant from a central longitudinal axis and a resilient configuration for squeezing into an oblong shape that is insertable into a surgical incision wherein said solid portion of said O-ring defines a first solid quadrant and a diagonally opposed second solid quadrant wherein said first solid quadrant includes a curved outer surface, a curved annular surface, and a sinusoidal surface, and said second solid quadrant includes a curved outer surface, a curved annular surface, and a sinusoidal surface; and
    two recesses that are selectively sized and shaped to enable a snap-action rolling of said O-ring about said cross-sectional center in predetermined increments.

2. An O-ring according to claim 1 wherein said at least one recess comprises at least one circumferential groove.

3. An O-ring according to claim 1 comprising a plurality of circumferentially positioned recesses.

4. An O-ring according to claim 1 wherein said at least one recess yields a cruciform cross-section of said O-ring.

5. An O-ring according to claim 1 wherein said first and second curved annular surfaces are at substantially the same radial distance from said central longitudinal axis, and are vertically oriented so as to be substantially parallel with said central longitudinal axis.

6. An adjustable surgical wound protector, comprising:
    an elongate open-ended tube formed of a pliable material that is impervious to solid and fluid contaminants for inserting lengthwise into a surgical incision;
    two O-rings, one each secured around the open ends of said tube having a resilient configuration for overlapping the inner edge of the wound and for squeezing into an oblong shape that is insertable with a lengthwise portion of the sleeve adjacent to one of said O-rings in said surgical incision; and
    wherein at least one O-ring comprises a circular cross-section of comprising four quadrants wherein material defining two diagonally opposed quadrants is removed, leaving two diagonally opposed recesses and at least one recess for enabling selected snap-action rolling of said at least one O-ring for rolling the remaining lengthwise portion of said sleeve on itself about said O-ring to shorten said sleeve in predetermined increments and to resist subsequent lengthening, whereby the sleeve length can be adjusted before or after placement in the wound; and further wherein said solid portion of said O-ring defines a first solid quadrant and a diagonally opposed second solid quadrant wherein said first solid quadrant includes a curved outer surface, a curved annular surface, and a sinusoidal surface, and said second solid quadrant includes a curved outer surface, a curved annular surface, and a sinusoidal surface.

7. An adjustable surgical wound protector according to claim 6 wherein said first and second curved annular surfaces are at substantially the same radial distance from said central longitudinal axis, and are vertically oriented so as to be substantially parallel with said central longitudinal axis.

8. An adjustable surgical wound protector according to claim 7 wherein said sinusoidal surfaces extend transversely relative to said central longitudinal axis.

9. An adjustable surgical wound protector according to claim 6 wherein said sleeve is a thin sheet disposed in a generally cylindrical form with overlapping lengthwise margins sealed together.

* * * * *